(12) United States Patent
Kale et al.

(10) Patent No.: US 11,718,644 B2
(45) Date of Patent: Aug. 8, 2023

(54) PURIFIED PROTEIN COMPOSITIONS AND METHODS OF PRODUCTION

(71) Applicant: Clara Foods Co., South San Francisco, CA (US)

(72) Inventors: Aniket Kale, Pleasanton, CA (US); Ranjan Patnaik, South San Francsico, CA (US)

(73) Assignee: CLARA FOODS CO., South San Francisco, CA (US)

( * ) Notice: Subject to any disclaimer, the term of this patent is extended or adjusted under 35 U.S.C. 154(b) by 0 days.

(21) Appl. No.: 18/050,213

(22) Filed: Oct. 27, 2022

(65) Prior Publication Data

US 2023/0073271 A1    Mar. 9, 2023

Related U.S. Application Data

(63) Continuation of application No. PCT/US2022/038074, filed on Jul. 22, 2022.

(60) Provisional application No. 63/225,410, filed on Jul. 23, 2021, provisional application No. 63/225,388, filed on Jul. 23, 2021.

(51) Int. Cl.
| | |
|---|---|
| *C07K 1/36* | (2006.01) |
| *B01D 15/36* | (2006.01) |
| *C07K 1/16* | (2006.01) |
| *B01D 61/16* | (2006.01) |

(52) U.S. Cl.
CPC .............. *C07K 1/36* (2013.01); *B01D 15/362* (2013.01); *B01D 15/363* (2013.01); *B01D 61/16* (2013.01); *C07K 1/16* (2013.01); *B01D 2311/04* (2013.01); *B01D 2311/2697* (2022.08)

(58) Field of Classification Search
CPC ... C07K 1/36; C07K 1/16; C07K 1/18; C07K 1/34; B01D 15/362; B01D 15/363; B01D 15/361; B01D 61/16; B01D 2311/04; B01D 2311/2626; B01D 2311/2697; C12N 1/14; C12N 1/16; C12N 1/165; C12N 15/10; C12N 15/80; C12N 15/81; C12N 15/815; C12N 2500/74; B01J 47/00; B01J 47/014; B01J 47/016; A23L 5/00; A23L 5/273; A23L 25/40; A23L 31/00; A23L 31/10; A23L 31/15; A61K 31/715; A61K 36/05
See application file for complete search history.

(56) References Cited

U.S. PATENT DOCUMENTS 7,205,018 B2   4/2007  Sherwood et al.
7,794,770 B2   9/2010  Sherwood et al.
(Continued)

FOREIGN PATENT DOCUMENTS

CN    102190722 A  *  9/2011  ........... C07K 14/765
WO    WO-9113982 A1    9/1991
(Continued)

OTHER PUBLICATIONS

Xiang et al, English translation of Patent Publication CN 10219722, Sep. 2011. (Year: 2011).*
(Continued)

*Primary Examiner* — Joseph W Drodge
(74) *Attorney, Agent, or Firm* — Fenwick & West LLP

(57) ABSTRACT

The present disclosure provides methods for producing consumable recombinant proteins that are substantially free from herein-disclosed undesired byproducts.

30 Claims, 8 Drawing Sheets

(56) References Cited

U.S. PATENT DOCUMENTS

| | | | |
|---|---|---|---|
| 7,799,363 | B2 | 9/2010 | Sherwood et al. |
| 7,842,326 | B2 | 11/2010 | Sherwood et al. |
| 7,897,192 | B2 | 3/2011 | Sherwood et al. |
| 7,906,160 | B2 | 3/2011 | Sherwood et al. |
| 9,220,292 | B2 | 12/2015 | Jenkins |
| 9,821,249 | B2 | 11/2017 | Oroskar et al. |
| 10,857,483 | B2 | 12/2020 | Oroskar et al. |
| 11,518,797 | B2 | 12/2022 | Anchel |
| 2008/0038753 | A1* | 2/2008 | Branum ............... C12N 9/1241 435/71.1 |
| 2015/0305390 | A1* | 10/2015 | Vrljic .................... A23L 13/424 426/574 |
| 2015/0351435 | A1* | 12/2015 | Fraser ...................... A23J 1/14 426/533 |
| 2016/0002694 | A1* | 1/2016 | Neerathilingam ....... C12N 1/20 435/252.33 |
| 2017/0188612 | A1* | 7/2017 | Varadan ................ A23L 13/422 |
| 2017/0295833 | A1* | 10/2017 | Fraser ...................... C12C 5/026 |
| 2018/0355020 | A1* | 12/2018 | Anchel .................. C07K 14/77 |
| 2021/0222214 | A1* | 7/2021 | Dietrich ............... C12N 9/0006 |
| 2021/0337826 | A1 | 11/2021 | Ivey et al. |
| 2022/0039443 | A1 | 2/2022 | Mahadevan et al. |
| 2023/0086338 | A1* | 3/2023 | Mahadevan ........... C07K 14/77 |

FOREIGN PATENT DOCUMENTS

| | | | |
|---|---|---|---|
| WO | WO-03037102 | A2 | 5/2003 |
| WO | WO2014008406 | A2 * | 1/2014 ............. A61K 39/02 |
| WO | WO-2015153666 | A1 | 10/2015 |
| WO | WO-2016077457 | A1 | 5/2016 |
| WO | WO-2021007565 | A1 | 1/2021 |
| WO | WO-2021034980 | A1 | 2/2021 |
| WO | WO-2021144342 | A1 | 7/2021 |
| WO | WO-2021158817 | A1 | 8/2021 |
| WO | WO-2022076615 | A1 | 4/2022 |
| WO | WO-2022182799 | A1 | 9/2022 |
| WO | WO-2023004153 | A1 | 1/2023 |
| WO | WO-2023004172 | A1 | 1/2023 |

OTHER PUBLICATIONS

Dupont Product Data Sheet, "DupontTM AmberLiteTM FPX66 Polymeric Adsobent", published Apr. 2021. (Year: 2012).*

Tripathi et al, "Recent Developments in Bioprocessing of Recombinant Proteins: Expression Hosts and Process Development", Frontiers in Bioengineering and Biotechnology, vol. 7, Article 420, published Dec. 20, 2019. (Year: 2019).*

Demain et al. Production of recombinant proteins by microbes and higher organisms. Biotechnology Advances, 27 (2009) 297-306. Available online Jan. 31, 2009.

PCT/US2022/038074 International Search Report and Written Opinion dated Oct. 21, 2022.

Upadhyay et al. Purification of recombinant ovalbumin from inclusion bodies of *Escherichia coli*. Protein Expr Purif (2015).

Järviö et al. Ovalbumin production using Trichoderma reesei culture and low-carbon energy could mitigate the environmental impacts of chicken-egg-derived ovalbumin. Nature Food, vol. 2, pp. 1005-1013 (2021).

* cited by examiner

PURIFIED PROTEIN COMPOSITIONS AND METHODS OF PRODUCTION

CROSS-REFERENCE TO RELATED APPLICATIONS

This application is a continuation of International Patent Application PCT/US22/38074, filed Jul. 22, 2022, which claims the benefit of U.S. Provisional Application No. 63/225,388, filed Jul. 23, 2021 and U.S. Provisional Application No. 63/225,410, filed Jul. 23, 2021, the contents of each of which is incorporated by reference in its entirety.

BACKGROUND

Ideally, compositions of consumable recombination proteins are free from undesired manufacturing ingredients, contaminants, and other microbial components and byproducts. In some instances, a recombinant microbial cell synthesizes measurable amounts of undesired byproducts and these must be isolated from the desired consumable recombination proteins when producing a commercial product. There remains an unmet need to produce consumable recombination proteins that are substantially free from such undesired byproducts.

SUMMARY

The present disclosure provides methods for producing consumable recombinant proteins that are substantially free from herein-disclosed undesired byproducts.

An aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an anionic resin that reversibly attaches to the recombinant protein and does not substantially attach to the plurality of recombinant cell byproducts; collecting the separated recombinant protein, thereby obtaining a protein product having a reduced quantity of the plurality of recombinant cell byproducts; and formulating a consumable composition comprising the protein product.

Another aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises one or more cation exchange resins that reversibly attach to the recombinant protein and do not substantially attach to the plurality of recombinant cell byproducts; collecting the separated recombinant protein, thereby obtaining a protein product having a reduced quantity of the plurality of recombinant cell byproducts; and formulating a consumable composition comprising the protein product.

A further aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an flocculant that reversibly attaches to one or more components of the plurality of recombinant cell byproducts and does not substantially attach to the recombinant protein; collecting the separated recombinant protein, thereby obtaining a protein product having a reduced quantity of the plurality of recombinant cell byproducts; and formulating a consumable composition comprising the protein product.

A further aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an adsorbent that reversibly attaches to one or more components of the plurality of recombinant cell byproducts and does not substantially attach to the recombinant protein; collecting the separated recombinant protein, thereby obtaining a protein product having a reduced quantity of the plurality of recombinant cell byproducts; and formulating a consumable composition comprising the protein product.

In an aspect, the present disclosure provides a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an enzyme that either digests the recombinant protein or digests the EPS; collecting the separated recombinant protein, thereby obtaining a protein product having a reduced quantity of the plurality of recombinant cell byproducts; and formulating a consumable composition comprising the protein product.

In another aspect, the present disclosure provides a consumable composition obtained by any herein disclosed method.

Additionally, any composition or method disclosed herein is applicable to any herein-disclosed composition or method. In other words, any aspect or embodiment described herein can be combined with any other aspect or embodiment as disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present disclosure provides methods for producing consumable recombinant proteins that are substantially free from herein-disclosed undesired byproducts.

It has been discovered that when recombinant proteins are produced by fermenting yeast cells, such as *Pichia*, the recombinant cells likewise produces recombinant cell byproducts. The recombinant cell byproduct component may be produced in an about equal proportion as the recombinant protein, e.g., when the recombinant cell byproduct is an exopolysaccharide (EPS). This results in lower concentration of the recombinant protein in a resulting protein product or consumable composition. In some cases, the presence of recombinant cell byproducts in a protein product or consumable composition may have a non-preferred taste. Moreover, the presence of recombinant cell byproduct in a protein product or consumable composition will have different properties, such as density, viscosity, gelling, and flavor, relative to a protein product or consumable composition that lacks the recombinant cell byproduct. Accordingly, methods for processing a composition comprising a recombinant protein and a recombinant cell byproduct, e.g., EPS and/or an off-flavor component to separate the recombinant protein and the recombinant cell byproduct is needed.

Resin-Based Purification

An aspect of the present disclosure is a method for preparing a protein product having a reduced quantity of a recombinant cell byproduct. The method comprises steps of: obtaining a composition comprising a recombinant protein and a recombinant cell byproduct; processing the composition under conditions that separate the recombinant protein and the recombinant cell byproduct, wherein the processing comprises a resin that reversibly attaches to the recombinant protein and does not substantially attach to the recombinant cell byproduct; and collecting the separated recombinant protein, thereby obtaining a protein product having a reduced quantity of the recombinant cell byproduct. In this method, the recombinant cell byproduct is an exopolysaccharide (EPS) or an off-flavor component.

Figure 1:
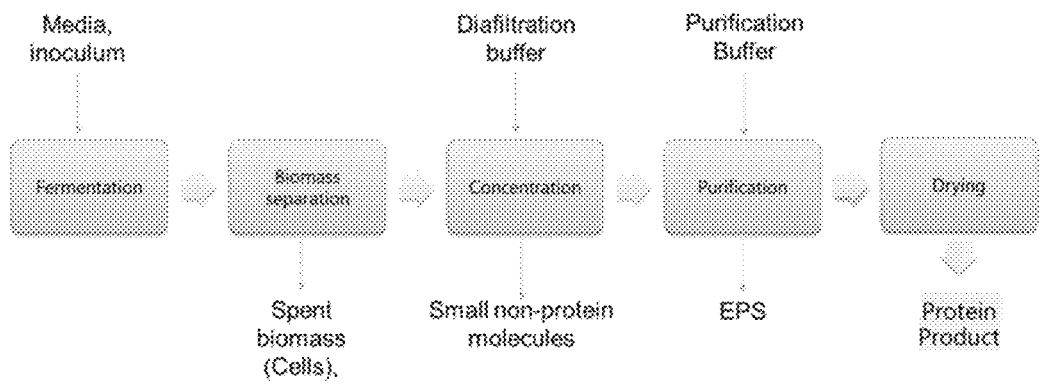
FIG. 1 to FIG. 10 are a flow diagrams illustrating method for producing a protein products or purified EPS of the present disclosure.

A illustrative method for producing a composition comprising a recombinant protein and a recombinant cell byproduct and separate the recombinant protein and the recombinant cell byproduct is shown in FIG. 1. The method of this aspect can be used to separate any extracellular product that is produced during a fermentation processes. The recombinant cell byproduct (e.g., EPS or off-flavor component) molecules are not ionic in nature and will flow through in an ion exchange column.

In embodiments, the resin is an anion exchanger or the resin is a cation exchange resin. In some cases, the cation exchanger is a strong cation exchange resin or a weak cation exchange resin. In some embodiments, the strong cation exchange resin is a sulphonate-type resin or the weak cation exchange resin is a carboxymethyl-type resin.

Any commercially-available resin that is capable of binding protein may be used.

An aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an anionic resin that reversibly attaches to the recombinant protein and does not substantially attach to the plurality of recombinant cell byproducts; collecting the separated recombinant protein, thereby obtaining a protein product having a reduced quantity of the plurality of recombinant cell byproducts; and formulating a consumable composition comprising the protein product.

In embodiments, wherein the composition comprising the recombinant protein and the plurality of recombinant cell byproducts is a cell culturing medium.

In some embodiments, wherein the composition comprising the recombinant protein and the plurality of recombinant cell byproducts is a cell culture medium comprising recombinant cells that secreted the recombinant protein and the plurality of recombinant cell byproducts.

In various embodiments, wherein the composition comprising the recombinant protein and the plurality of recombinant cell byproducts lacks recombinant cells that secreted the recombinant protein and the plurality of recombinant cell byproducts.

In several embodiments, wherein the composition comprising the recombinant protein and the plurality of recombinant cell byproducts has a pH greater than the isoelectric point (pI) of the recombinant protein.

In embodiments, wherein the pH of the composition comprising the recombinant protein and the plurality of recombinant cell byproducts is not modified to achieve a pH greater than the pI of the recombinant protein.

In some embodiments, wherein the anion resin is a strong anion exchange resin or a weak anion exchange resin.

In various embodiments, wherein the anion resin is one or more of Capto Q resin, a DEAE type weak anion exchanger, a resin with trimethyl aminoethyl groups, a resin with triethyl aminoethyl groups, a resin with quaternary amine groups.

In several embodiments, wherein the anion resin is a component of a chromatography system.

In embodiments, wherein the chromatography system operates in batch mode with an axial flow column or a radial flow column or a centrifugal column or by use of a membrane chromatography column.

In some embodiments, wherein the chromatography system operates in a continuous mode comprising multiple columns in parallel, with the feed to the columns being switchable such that various steps in a chromatography process (e.g., equilibration, load, elute, and clean), occur contemporaneously.

In various embodiments, wherein the continuous mode comprises a simulated moving bed (SMB) or an Ion Separator (e.g., ISEP®) system.

In several embodiments, wherein the composition comprising the recombinant protein and the plurality of recombinant cell byproducts was previously treated to remove spent biomass including recombinant cells and/or was previously treated to remove small non-protein molecules.

In embodiments, wherein the treatment to remove small non-protein molecules comprises a step that concentrates the composition comprising the recombinant protein and the plurality of recombinant cell byproducts.

In some embodiments, wherein the treatment to remove small non-protein molecules comprises a diafiltration buffer.

In various embodiments, The method further comprises a concentration step and/or diafiltration treatment of the separated recombinant protein to produce a protein-containing composition having a preferred pH and/or ionic condition.

In several embodiments, wherein the protein-containing composition having a preferred pH and/or ionic condition is further heat treated and/or dried.

In embodiments, wherein the composition comprising the recombinant protein and the plurality of recombinant cell byproducts and/or the protein product having a reduced quantity of the plurality of recombinant cell byproducts is further heat treated and/or dried.

In some embodiments, wherein the heat treatment separates the recombinant protein and the off-flavor component, wherein the heat is applied at a temperature and duration such that the off-flavor component is volatized and a gaseous off-flavor component is removable.

In various embodiments, wherein a vacuum is applied contemporaneous with the application of heat and the vacuum facilitates removal of the gaseous off-flavor component.

In several embodiments, wherein the off-flavor component is an acid, an alcohol, an aldehyde, an aromatic, an ester, or a ketone.

In embodiments, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

In some embodiments, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

In various embodiments, wherein the method comprises agitation during the heat treatment.

In several embodiments, wherein the heat treatment and/or drying step produces a dry protein product having a reduced quantity of the plurality of recombinant cell byproducts.

In embodiments, wherein the composition comprising the recombinant protein and the plurality of recombinant cell byproducts and/or the protein product having a reduced quantity of the plurality of recombinant cell byproducts further undergoes an oxidation step, e.g., comprising the addition of hydrogen peroxide.

In some embodiments, wherein the ratio of the recombinant cell byproducts to recombinant protein in the composition comprising a recombinant protein and the plurality of recombinant cell byproducts is about 1:3 to about 3:1.

In various embodiments, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

In several embodiments, wherein less than about 10% of the weight of the protein product comprises recombinant cell byproducts.

In embodiments, wherein less than about 5% of the weight of the protein product comprises recombinant cell byproducts.

In some embodiments, wherein less than about 5%, less than about 1%, less than about 0.1%, or less than about 0.01% of the weight of the protein product comprises the off-flavor component.

In various embodiments, wherein the off-flavor component in the protein product is virtually undetectable to a standard consumer.

In several embodiments, wherein the EPS is generally inseparable from the recombinant protein when using size exclusion chromatography.

In embodiments, wherein the EPS is naturally a component of a recombinant cell's cell wall.

In some embodiments, wherein the EPS has an apparent size of about 13 kDa to about 27 kDa as characterized by a size exclusion chromatography column.

In various embodiments, wherein the EPS comprises mannose.

In several embodiments, wherein the EPS further comprises N-acetylglucosamine and/or glucose.

In embodiments, wherein the EPS comprises about 91 mol % mannose, about 5 mol % N-acetylglucosamine, and about 3 mol % glucose as analyzed by gas chromatography in tandem with mass spectrometry.

In some embodiments, wherein the EPS comprises an α(1,6)-linked backbone with α(1,2)-linked branches and/or α(1,3)-linked branches.

In various embodiments, wherein the EPS is a mannan.

In several embodiments, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

In embodiments, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

In some embodiments, wherein the fungus is a *Pichia* species.

In various embodiments, wherein the *Pichia* species is *Komagataella phaffii* or *Komagataella pastoris*.

In several embodiments, wherein the recombinant protein is an enzyme, a nutritive protein, a food ingredient, or a food additive.

In embodiments, wherein the enzyme is pepsinogen or pepsin.

In some embodiments, wherein the protein is an egg-white protein.

In various embodiments, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

In several embodiments, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

In embodiments, wherein the consumable composition comprising the protein product comprises food products, beverage products, or dietary supplements.

In some embodiments, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

In various embodiments, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

In several embodiments, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

In embodiments, wherein the processing the composition under conditions that separate the recombinant protein from the plurality of recombinant cell byproducts further comprises one or more of: i) one or more cation exchange resin that reversibly attach to the recombinant protein and does not substantially attach to the EPS, ii) an enzyme that digests the recombinant protein or the EPS, iii) an adsorbent that reversibly attaches to the EPS and does not substantially attach to the recombinant protein, and/or iv) a flocculant that attaches to the EPS and does not substantially attach to the recombinant protein.

In another aspect, the present disclosure provides a consumable composition obtained by any above-disclosed method.

Another aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises one or more cation exchange resins that reversibly attach to the recombinant protein and do not substantially attach to the plurality of recombinant cell byproducts; collecting the separated recombinant protein, thereby obtaining a protein product having a reduced quantity of the plurality of recombinant cell byproducts; and formulating a consumable composition comprising the protein product.

In some embodiments, wherein the one or more cation exchange resins comprise a strong cation exchange resin, e.g., a sulfopropyl-, sulfomethyl-, or sulphonate-type resin, and/or a weak cation exchange resin, e.g., a carboxymethyl-type resin.

In various embodiments, wherein the one or more cation exchange resins comprise poly styrene divinyl benzene, poly methacrylate or cellulose or cross-linked dextran or cross-linked agarose or inorganic materials coated with hydrophilic polymers.

In several embodiments, wherein the one or more cation exchange resins have a particle size of from about 50 μm and about 200 μm and/or have a protein binding capacity of from about 50 to about 100 g protein/L resin.

In embodiments, wherein the one or more cation exchange resins comprise Cytiva Capto S, HP20, resindion SP400, Sepragen S, SP20, and/or Mitsubishi Relisorb EXE349.

In some embodiments, wherein the processing step comprises two cationic resins, wherein the two cationic resins are in a ratio of 1:5 to 5:1, 1:4 to 4:1, 1:3 to 3:1, 1:2 to 2:1, or 1:1.

In various embodiments, wherein the two resins are SP400 and Sepragen S and in a ratio of about 3:1, e.g., 2.75:1.25.

In several embodiments, wherein the composition comprising the recombinant protein and the plurality of recombinant cell byproducts lacks recombinant cells that secreted the recombinant protein and the plurality of recombinant cell byproducts.

In embodiments, wherein the composition comprising the recombinant protein and the plurality of recombinant cell byproducts has a pH less than the isoelectric point (pI) of the recombinant protein, which is achieved by lowering the pH of the composition comprising the recombinant protein and the plurality of recombinant cell byproducts.

In some embodiments, wherein the one or more cationic resins are components of a chromatography system, wherein the chromatography system operates in batch mode with an axial flow column or a radial flow column or a centrifugal column or by use of a membrane chromatography column.

In various embodiments, wherein the one or more cationic resins are components of a chromatography system, wherein the chromatography system operates in a continuous mode comprising multiple columns in parallel, with the feed to the columns being switchable such that various steps in a chromatography process (e.g., equilibration, load, elute, and clean), occur contemporaneously.

In several embodiments, wherein the continuous mode comprises a simulated moving bed (SMB) or an Ion Separator (e.g., ISEP®) system.

In embodiments, wherein the composition comprising the recombinant protein and the plurality of recombinant cell byproducts was previously treated to remove spent biomass including recombinant cells and/or was previously treated to remove small non-protein molecules.

In some embodiments, wherein the treatment to remove small non-protein molecules comprises a step that concentrates the composition comprising the recombinant protein and the plurality of recombinant cell byproducts.

In various embodiments, wherein the treatment to remove small non-protein molecules comprises a diafiltration buffer.

In several embodiments, the method further comprises a concentration step and/or diafiltration treatment of the separated recombinant protein to produce a protein-containing composition having a preferred pH and/or ionic condition.

In embodiments, wherein the protein-containing composition having a preferred pH and/or ionic condition is further heat treated and/or dried.

In some embodiments, wherein the composition comprising the recombinant protein and the plurality of recombinant cell byproducts and/or the protein product having a reduced quantity of the plurality of recombinant cell byproducts is further heat treated and/or dried.

In various embodiments, wherein the heat treatment separates the recombinant protein and the off-flavor component, wherein the heat is applied at a temperature and duration such that the off-flavor component is volatized and a gaseous off-flavor component is removable.

In several embodiments, wherein a vacuum is applied contemporaneous with the application of heat and the vacuum facilitates removal of the gaseous off-flavor component.

In embodiments, wherein the off-flavor component is an acid, an alcohol, an aldehyde, an aromatic, an ester, or a ketone.

In some embodiments, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

In various embodiments, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

In several embodiments, wherein the method comprises agitation during the heat treatment.

In embodiments, wherein the heat treatment and/or drying step produces a dry protein product having a reduced quantity of the plurality of recombinant cell byproducts.

In some embodiments, wherein the composition comprising the recombinant protein and the plurality of recombinant cell byproducts and/or the protein product having a reduced quantity of the plurality of recombinant cell byproducts further undergoes an oxidation step, e.g., comprising the addition of hydrogen peroxide.

In various embodiments, wherein the ratio of the recombinant cell byproducts to recombinant protein in the composition comprising a recombinant protein and the plurality of recombinant cell byproducts is about 1:3 to about 3:1.

In several embodiments, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

In embodiments, wherein less than about 10% of the weight of the protein product comprises recombinant cell byproducts.

In some embodiments, wherein less than about 5% of the weight of the protein product comprises recombinant cell byproducts.

In various embodiments, wherein less than about 5%, less than about 1%, less than about 0.1%, or less than about 0.01% of the weight of the protein product comprises the off-flavor component.

In several embodiments, wherein the off-flavor component in the protein product is virtually undetectable to a standard consumer.

In embodiments, wherein the EPS is generally inseparable from the recombinant protein when using size exclusion chromatography.

In some embodiments, wherein the EPS is naturally a component of a recombinant cell's cell wall.

In various embodiments, wherein the EPS has an apparent size of about 13 kDa to about 27 kDa as characterized by a size exclusion chromatography column.

In several embodiments, wherein the EPS comprises mannose.

In embodiments, wherein the EPS further comprises N-acetylglucosamine and/or glucose.

In some embodiments, wherein the EPS comprises about 91 mol % mannose, about 5 mol % N-acetylglucosamine, and about 3 mol % glucose as analyzed by gas chromatography in tandem with mass spectrometry.

In various embodiments, wherein the EPS comprises an α(1,6)-linked backbone with α(1,2)-linked branches and/or α(1,3)-linked branches.

In several embodiments, wherein the EPS is a mannan.

In embodiments, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

In some embodiments, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

In various embodiments, wherein the fungus is a *Pichia* species.

In several embodiments, wherein the *Pichia* species is *Komagataella phaffii* or *Komagataella pastoris*.

In embodiments, wherein the recombinant protein is an enzyme, a nutritive protein, a food ingredient, or a food additive.

In some embodiments, wherein the enzyme is pepsinogen or pepsin.

In various embodiments, wherein the protein is an egg-white protein.

In several embodiments, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

In embodiments, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

In some embodiments, wherein the consumable composition comprising the protein product comprises food products, beverage products, or dietary supplements.

In various embodiments, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

In several embodiments, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

In embodiments, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

In some embodiments, wherein the processing the composition under conditions that separate the recombinant protein from the plurality of recombinant cell byproducts further comprises one or more of: i) an anionic resin that reversibly attaches to the recombinant protein and does not substantially attach to the EPS, ii) an enzyme that digests the recombinant protein or the EPS, iii) an adsorbent that reversibly attaches to the EPS and does not substantially attach to the recombinant protein, and/or iv) a flocculant that attaches to the EPS and does not substantially attach to the recombinant protein.

In another aspect, the present disclosure provides a consumable composition obtained by any above-disclosed method.

In various embodiments, the resin is a component of a chromatography system. In some cases, the chromatography system operates in batch mode with an axial flow column or a radial flow column or a centrifugal column or by use of a membrane chromatography column or the chromatography system operates in a continuous mode comprising multiple columns in parallel, with the feed to the columns being switchable such that various steps in a chromatography process (e.g., equilibration, load, elute, and clean), occur contemporaneously. In various cases, the continuous mode comprises a simulated moving bed (SMB) or an Ion Separator (e.g., ISEP®) system.

In embodiments, the composition comprising a recombinant protein and a recombinant cell byproduct was previously treated to remove spent biomass including recombinant cells and was previously treated to remove small non-protein molecules. In some cases, the treatment to remove small non-protein molecules comprises a step that concentrates the composition comprising the recombinant protein and the recombinant cell byproduct. In embodiments, the treatment to remove small non-protein molecules comprises a diafiltration buffer.

In some embodiments, the method further comprises a concentration step and/or diafiltration treatment of the separated recombinant protein to produce a protein-containing composition having a preferred pH and/or ionic conditions. In embodiments, protein-containing composition having a preferred pH and/or ionic conditions is further heat treated and/or dried.

Figure 11:
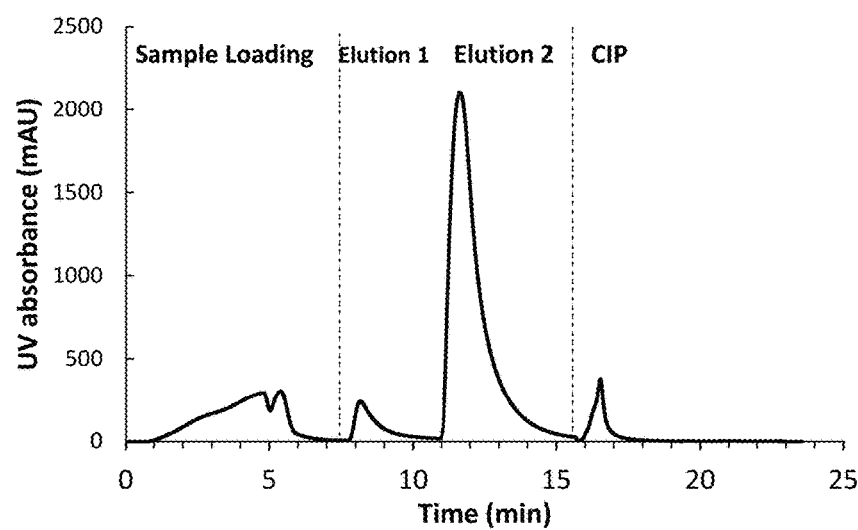
FIG. 11 is a chromatogram showing separation of recombinant proteins using a typical ion exchange resin listed above. Black line is the absorbance trace at 280 nm indicating the proteins.

An illustrative chromatogram showing the purification of a recombinant protein using a cation exchange column SP400 is shown in FIG. 11. The recombinant proteins are bound to the column eluted in Elution Zones 1 and 2 (beginning at 8 minutes and 11 minutes, respectively). More specifically, the fraction in Elution Zone 2 is the recombinant protein of interest separated from the unbound peak during loading (around 5 minutes), bound product peak during clean-in-place (CIP; around 16 minutes), and the other loosely bound proteins in Elution Zone 1 (around 8 minutes).

In some embodiments, a variation of the process shown in FIG. 1 would be to equilibrate the column in the elution buffer 1 pre feed application to elute the host cell proteins along with the recombinant cell byproduct impurities, e.g., EPS or off-flavor component.

In another variation of the process shown in FIG. 1, the concentration step is omitted, and a microfiltered fermentation supernatant is loaded onto the column that is equilibrated in elution 1 buffer; thereby separating the recombinant cell byproduct (e.g., EPS or off-flavor component), small molecule impurities and the host cell proteins in the column loading step.

Processes for protein separation and intracellular protein separation have been described in the literature, see, e.g., U.S. Pat. Nos. 10,857,483 and 9,821,249; the contents of each of which is incorporated herein by reference in its entirety.

Hydrophobic Solvent or Amphiphatic Solvent-Based Purification

An aspect of the present disclosure is a method for preparing a protein product having a reduced quantity of a recombinant cell byproduct. The method comprises steps of: obtaining a composition comprising a recombinant protein and a recombinant cell byproduct; processing the composition under conditions that separate the recombinant protein and the recombinant cell byproduct; collecting the separated recombinant protein, thereby obtaining a protein product having a reduced quantity of the recombinant cell byproduct. In this method the recombinant cell byproduct is an off-flavor component. In embodiments, the step of processing the composition comprises use of a hydrophobic solvent or an amphiphatic solvent which separates the recombinant protein and the recombinant cell byproduct.

Figure 6:
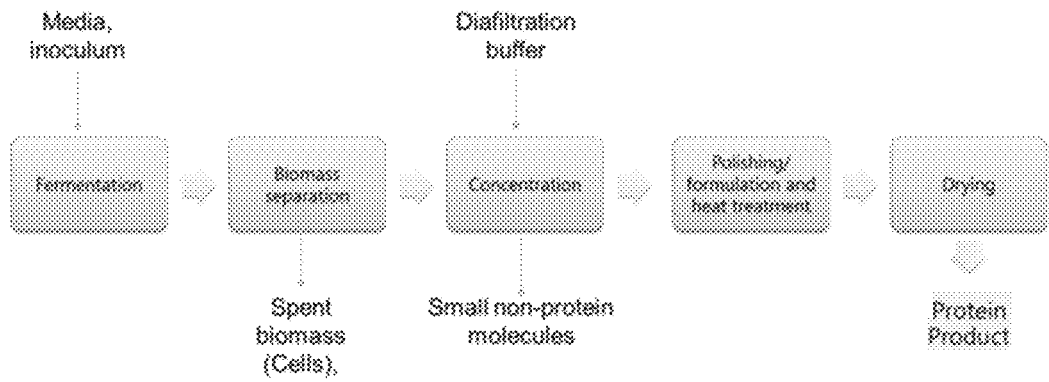

A illustrative method for producing a composition comprising a recombinant protein and a recombinant cell byproduct and separate the recombinant protein and the recombinant cell byproduct is shown in FIG. 6.

In embodiments, the composition comprising the recombinant protein and the recombinant cell byproduct was produced by fermentation of the recombinant cell.

In some embodiments, the composition comprising the recombinant protein and the recombinant cell byproduct was previously treated to remove spent biomass including recombinant cells.

In various embodiments, the composition comprising the recombinant protein and the recombinant cell byproduct was previously treated to remove small non-protein molecules.

In some cases, the treatment to remove small non-protein molecules comprises a diafiltration buffer. The treatment to remove small non-protein molecules may comprise a step that concentrates the composition comprising the recombinant protein and the recombinant cell byproduct.

In some embodiments, the method further comprises a concentration step and/or diafiltration treatment of the separated recombinant protein to produce a protein-containing composition having a preferred pH and/or ionic conditions. In some cases, protein-containing composition having a preferred pH and/or ionic conditions is further heat treated and/or dried. The heat treatment and/or drying step may produce a dry protein product having a reduced quantity of the off-flavor component.

In various embodiments, the protein product having a reduced quantity of the off-flavor component comprises an at least 50% reduction in off-flavor component quantity relative to the composition comprising a recombinant protein and a recombinant cell byproduct. In some cases, the protein product has an at least 75% reduction, at least 80% reduction, at least 90% reduction, or at least 95% reduction in the off-flavor component relative to the composition comprising a recombinant protein and a recombinant cell byproduct.

In embodiments, less than about 5%, less than about 1%, less than about 0.1%, or less than about 0.01% of the weight of the protein product comprises the off-flavor component. In some cases, the off-flavor component in the protein product is virtually undetectable to a standard consumer.

Enzyme-Based Purification

In an aspect, the present disclosure provides a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an enzyme that either digests the recombinant protein or digests the EPS; collecting the separated recombinant protein, thereby obtaining a protein product having a reduced quantity of the plurality of recombinant cell byproducts; and formulating a consumable composition comprising the protein product.

In embodiments, wherein the composition comprising the recombinant protein and the plurality of recombinant cell byproducts is a cell culturing medium.

Figure 2:
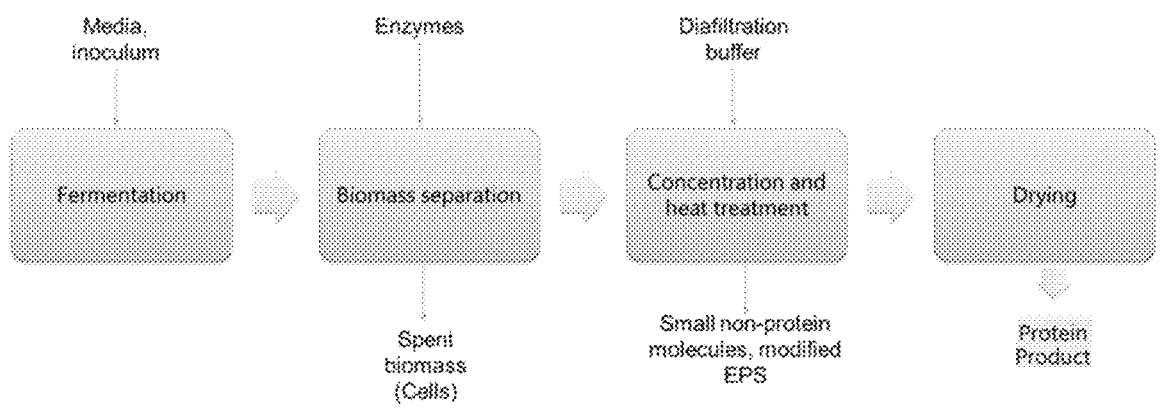

A illustrative method for producing a composition comprising a recombinant protein and a recombinant cell byproduct and separate the recombinant protein and the recombinant cell byproduct is shown in FIG. 2. The method of this aspect can be used to separate any extracellular product that is produced during a fermentation processes.

In embodiments, the enzyme either digests the recombinant protein or digests the recombinant cell byproduct.

In some embodiments, wherein the composition comprising the recombinant protein and the plurality of recombinant cell byproducts is a cell culture medium comprising recombinant cells that secreted the recombinant protein and the plurality of recombinant cell byproducts.

In various embodiments, wherein the composition comprising the recombinant protein and the plurality of recombinant cell byproducts lacks recombinant cells that secreted the recombinant protein and the plurality of recombinant cell byproducts.

In several embodiments, wherein the composition comprising the recombinant protein and the plurality of recombinant cell byproducts has a pH greater than the isoelectric point (pI) of the recombinant protein.

In embodiments, wherein the pH of the composition comprising the recombinant protein and the plurality of recombinant cell byproducts is not modified to achieve a pH greater than the pI of the recombinant protein.

In some embodiments, wherein the pH of the composition comprising the recombinant protein and the plurality of recombinant cell byproducts is modified to achieve a pH greater than the pI of the recombinant protein.

In various embodiments, wherein the pH of the composition comprising the recombinant protein and the plurality of recombinant cell byproducts is about 6.

In several embodiments, wherein the composition comprising the recombinant protein and the plurality of recombinant cell byproducts has a pH less than the isoelectric point (pI) of the recombinant protein.

In embodiments, wherein the pH of the composition comprising the recombinant protein and the plurality of recombinant cell byproducts achieved by lowering the pH.

In some embodiments, wherein the enzyme that digests the recombinant protein is pepsin or trypsin.

In various embodiments, wherein the digested recombinant protein permeates through an ultrafiltration system with a 10 kDa membrane.

In several embodiments, wherein the enzyme that digests the EPS is a mannase, a cellulase, or glucanase.

In embodiments, wherein undigested recombinant protein is concentrated by ultrafiltration system with a 5 kDa membrane.

In some embodiments, wherein the processing the composition under conditions that separate the recombinant protein from the plurality of recombinant cell byproducts further comprises a chromatography system.

In various embodiments, wherein the chromatography system operates in batch mode with an axial flow column or a radial flow column or a centrifugal column or by use of a membrane chromatography column.

In several embodiments, wherein the chromatography system operates in a continuous mode comprising multiple columns in parallel, with the feed to the columns being switchable such that various steps in a chromatography process (e.g., equilibration, load, elute, and clean), occur contemporaneously.

In embodiments, wherein the continuous mode comprises a simulated moving bed (SMB) or an Ion Separator (e.g., ISEP®) system.

In some embodiments, wherein the composition comprising the recombinant protein and the plurality of recombinant cell byproducts was previously treated to remove spent biomass including recombinant cells and/or was previously treated to remove small non-protein molecules.

In various embodiments, wherein the treatment to remove small non-protein molecules comprises a step that concentrates the composition comprising the recombinant protein and the plurality of recombinant cell byproducts.

In several embodiments, wherein the treatment to remove small non-protein molecules comprises a diafiltration buffer.

In embodiments, the method further comprises a concentration step and/or dia-filtration treatment of the separated recombinant protein to produce a protein-containing composition having a preferred pH and/or ionic condition.

In some embodiments, wherein the protein-containing composition having a preferred pH and/or ionic condition is further heat treated and/or dried.

In various embodiments, wherein the composition comprising the recombinant protein and the plurality of recombinant cell byproducts and/or the protein product having a reduced quantity of the plurality of recombinant cell byproducts is further heat treated and/or dried.

In several embodiments, wherein the heat treatment separates the recombinant protein and the off-flavor component, wherein the heat is applied at a temperature and duration such that the off-flavor component is volatized and a gaseous off-flavor component is removable.

In embodiments, wherein a vacuum is applied contemporaneous with the application of heat and the vacuum facilitates removal of the gaseous off-flavor component.

In some embodiments, wherein the off-flavor component is an acid, an alcohol, an aldehyde, an aromatic, an ester, or a ketone.

In various embodiments, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

In several embodiments, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

In embodiments, wherein the method comprises agitation during the heat treatment.

In some embodiments, wherein the heat treatment and/or drying step produces a dry protein product having a reduced quantity of the plurality of recombinant cell byproducts.

In various embodiments, wherein the composition comprising the recombinant protein and the plurality of recombinant cell byproducts and/or the protein product having a reduced quantity of the plurality of recombinant cell byproducts further undergoes an oxidation step.

In several embodiments, wherein the oxidization step comprises the addition of hydrogen peroxide.

In embodiments, wherein the ratio of the recombinant cell byproducts to recombinant protein in the composition comprising a recombinant protein and the plurality of recombinant cell byproducts is about 1:3 to about 3:1.

In some embodiments, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

In various embodiments, wherein less than about 10% of the weight of the protein product comprises recombinant cell byproducts.

In several embodiments, wherein less than about 5% of the weight of the protein product comprises recombinant cell byproducts.

In embodiments, wherein less than about 5%, less than about 1%, less than about 0.1%, or less than about 0.01% of the weight of the protein product comprises the off-flavor component.

In some embodiments, wherein the off-flavor component in the protein product is virtually undetectable to a standard consumer.

In various embodiments, wherein the EPS is generally inseparable from the recombinant protein when using size exclusion chromatography.

In several embodiments, wherein the EPS is naturally a component of a recombinant cell's cell wall.

In embodiments, wherein the EPS has an apparent size of about 13 kDa to about 27 kDa as characterized by a size exclusion chromatography column.

In some embodiments, wherein the EPS comprises mannose.

In various embodiments, wherein the EPS further comprises N-acetylglucosamine and/or glucose.

In several embodiments, wherein the EPS comprises about 91 mol % mannose, about 5 mol % N-acetylglucosamine, and about 3 mol % glucose as analyzed by gas chromatography in tandem with mass spectrometry.

In embodiments, wherein the EPS comprises an $\alpha(1,6)$-linked backbone with $\alpha(1,2)$-linked branches and/or $\alpha(1,3)$-linked branches.

In some embodiments, wherein the EPS is a mannan.

In various embodiments, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

In several embodiments, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma* vireus.

In embodiments, wherein the fungus is a *Pichia* species.

In some embodiments, wherein the *Pichia* species is *Komagataella phaffii* or *Komagataella pastoris*.

In various embodiments, wherein the recombinant protein is an enzyme, a nutritive protein, a food ingredient, or a food additive.

In several embodiments, wherein the enzyme is pepsinogen or pepsin.

In embodiments, wherein the protein is an egg-white protein.

In some embodiments, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

In various embodiments, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

In several embodiments, wherein the consumable composition comprising the protein product comprises food products, beverage products, or dietary supplements.

In embodiments, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

In some embodiments, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

In various embodiments, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

In several embodiments, wherein the processing the composition under conditions that separate the recombinant protein from the plurality of recombinant cell byproducts further comprises one or more of: i) a cationic resin that reversibly attaches to the recombinant protein and does not substantially attach to the EPS, ii) an anionic resin that reversibly attaches to the recombinant protein and does not substantially attach to the EPS, iii) a flocculant that attaches to the EPS and does not substantially attach to the recombinant protein, and/or iv) an adsorbent that attaches to the EPS and does not substantially attach to the recombinant protein.

In another aspect, the present disclosure provides a consumable composition obtained by any above-disclosed method.

Heat-Based Purification

An aspect of the present disclosure is a method for preparing a protein product having a reduced quantity of a recombinant cell byproduct. The method comprises steps of: obtaining a composition comprising a recombinant protein and a recombinant cell byproduct; processing the composition under conditions that separate the recombinant protein and the recombinant cell byproduct; collecting the separated recombinant protein, thereby obtaining a protein product having a reduced quantity of the recombinant cell byproduct. In this method the recombinant cell byproduct is an off-flavor component. In various embodiments, the step of processing the composition comprises use of heat which separates the recombinant protein and the recombinant cell byproduct, wherein the heat is applied at a temperature and duration such that the recombinant cell byproduct is volatized and a gaseous recombinant cell byproduct is removable.

A illustrative method for producing a composition comprising a recombinant protein and a recombinant cell byproduct and separate the recombinant protein and the recombinant cell byproduct is shown in FIG. 6.

In embodiments, the composition may be agitated while the heat is applied.

In some embodiments, a vacuum may be applied contemporaneous with an application of heat. In some cases, the vacuum facilitates removal of the gaseous recombinant cell byproduct.

In various cases, the temperature is up to 80° C.

In embodiments, the composition comprising the recombinant protein and the recombinant cell byproduct was produced by fermentation of the recombinant cell.

In some embodiments, the composition comprising the recombinant protein and the recombinant cell byproduct was previously treated to remove spent biomass including recombinant cells.

In various embodiments, the composition comprising the recombinant protein and the recombinant cell byproduct was previously treated to remove small non-protein molecules. In some cases, the treatment to remove small non-protein molecules comprises a diafiltration buffer. The treatment to remove small non-protein molecules may comprise a step that concentrates the composition comprising the recombinant protein and the recombinant cell byproduct.

In some embodiments, the method further comprises a concentration step and/or diafiltration treatment of the separated recombinant protein to produce a protein-containing composition having a preferred pH and/or ionic conditions. In some cases, protein-containing composition having a preferred pH and/or ionic conditions is further heat treated and/or dried. The heat treatment and/or drying step may produce a dry protein product having a reduced quantity of the off-flavor component.

In various embodiments, the protein product having a reduced quantity of the off-flavor component comprises an at least 50% reduction in off-flavor component quantity relative to the composition comprising a recombinant protein and a recombinant cell byproduct. In some cases, the protein product has an at least 75% reduction, at least 80% reduction, at least 90% reduction, or at least 95% reduction in the off-flavor component relative to the composition comprising a recombinant protein and a recombinant cell byproduct.

In embodiments, less than about 5%, less than about 1%, less than about 0.1%, or less than about 0.01% of the weight of the protein product comprises the off-flavor component. In some cases, the off-flavor component in the protein product is virtually undetectable to a standard consumer.

Adsorbent-Based Purification

A further aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an adsorbent that reversibly attaches to one or more components of the plurality of recombinant cell byproducts and does not substantially attach to the recombinant protein; collecting the separated recombinant protein, thereby obtaining a protein product having a reduced quantity of the plurality of recombinant cell byproducts; and formulating a consumable composition comprising the protein product.

Figure 3:
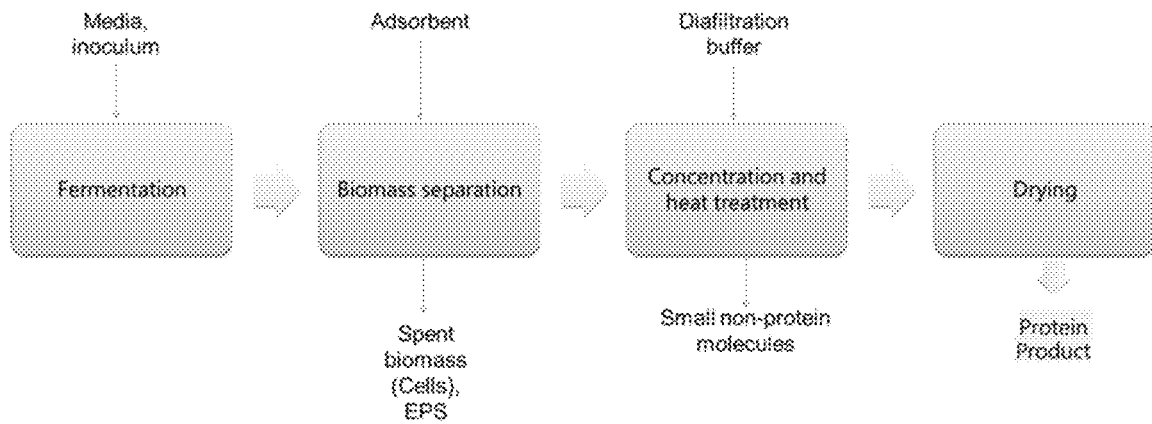

A illustrative method for producing a composition comprising a recombinant protein and a recombinant cell byproduct and separate the recombinant protein and the recombinant cell byproduct is shown in FIG. 3. The method of this aspect can be used to separate any extracellular product that is produced during a fermentation processes.

In embodiments, wherein the composition comprising the recombinant protein and the plurality of recombinant cell byproducts is a cell culturing medium.

In some embodiments, wherein the composition comprising the recombinant protein and the plurality of recombinant cell byproducts is a cell culture medium comprising recombinant cells that secreted the recombinant protein and the plurality of recombinant cell byproducts.

In various embodiments, wherein the composition comprising the recombinant protein and the plurality of recombinant cell byproducts has a pH greater than the isoelectric point (pI) of the recombinant protein.

In several embodiments, wherein the pH of the composition comprising the recombinant protein and the plurality of recombinant cell byproducts is not modified to achieve a pH greater than the pI of the recombinant protein.

In embodiments, wherein the adsorbent is added to a culturing medium comprising recombinant cells that are secreting the recombinant protein and the plurality of recombinant cell byproducts.

In some embodiments, wherein once the adsorbent attaches to one or more components of the plurality of recombinant cell byproducts, the adsorbent is separated from the recombinant protein.

In various embodiments, wherein when the adsorbent attaches to one or more components of the plurality of recombinant cell byproducts is isolated from the recombinant protein with a strainer, a filtering apparatus, and/or by centrifugation.

In several embodiments, the method further comprises supplementing the culturing medium again with a adsorbent.

In embodiments, wherein the adsorbent is provided to a biomass separation feed tank and to one or more components of the plurality of recombinant cell byproducts contemporaneously with removal of spent biomass including recombinant cells.

In some embodiments, wherein the adsorbent is provided after removal of spent biomass including recombinant cells.

In various embodiments, wherein the composition comprising the recombinant protein and the plurality of recombinant cell byproducts lacks recombinant cells that secreted the recombinant protein and the plurality of recombinant cell byproducts.

In several embodiments, wherein adsorbent comprises a resin and/or a hydrophobic adsorbent e.g., comprising a methacrylate or a silica backbone or is a DEAE type weak anion exchanger.

In embodiments, wherein the adsorbent is Dow Amberlite SD2, Mitsubishi Diaion HP20, Celite 545, Bentonite BE125, DIAION HPA25L, Chitosan 85% deacetylated, EZ DE, ultrapure diatomaceous earth, or Relisorb SP400.

In some embodiments, wherein the adsorbent is provided in a column, e.g., and operated in batch mode with an axial flow column or a radial flow column or a centrifugal column or by use of a membrane chromatography column.

In various embodiments, wherein the processing the composition under conditions that separate the recombinant protein from the plurality of recombinant cell byproducts further comprises a chromatography system.

In several embodiments, wherein the chromatography system operates in batch mode with an axial flow column or a radial flow column or a centrifugal column or by use of a membrane chromatography column or the chromatography system operates in a continuous mode comprising multiple columns in parallel, with the feed to the columns being switchable such that various steps in a chromatography process (e.g., equilibration, load, elute, and clean), occur contemporaneously.

In embodiments, wherein the continuous mode comprises a simulated moving bed (SMB) or an Ion Separator (e.g., ISEP®) system.

In some embodiments, wherein the composition comprising the recombinant protein and the plurality of recombinant cell byproducts was previously treated to remove spent biomass including recombinant cells and/or was previously treated to remove small non-protein molecules.

In various embodiments, wherein the treatment to remove small non-protein molecules comprises a step that concentrates the composition comprising the recombinant protein and the plurality of recombinant cell byproducts.

In several embodiments, wherein the treatment to remove small non-protein molecules comprises a diafiltration buffer.

In embodiments, the method further comprises a concentration step and/or dia-filtration treatment of the separated recombinant protein to produce a protein-containing composition having a preferred pH and/or ionic condition.

In some embodiments, wherein the protein-containing composition having a preferred pH and/or ionic condition is further heat treated and/or dried.

In various embodiments, wherein the composition comprising the recombinant protein and the plurality of recombinant cell byproducts and/or the protein product having a reduced quantity of the plurality of recombinant cell byproducts is further heat treated and/or dried.

In several embodiments, wherein the heat treatment separates the recombinant protein and the off-flavor component, wherein the heat is applied at a temperature and duration such that the off-flavor component is volatized and a gaseous off-flavor component is removable.

In embodiments, wherein a vacuum is applied contemporaneous with the application of heat and the vacuum facilitates removal of the gaseous off-flavor component.

In some embodiments, wherein the off-flavor component is an acid, an alcohol, an aldehyde, an aromatic, an ester, or a ketone.

In various embodiments, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

In several embodiments, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

In embodiments, wherein the method comprises agitation during the heat treatment.

In some embodiments, wherein the heat treatment and/or drying step produces a dry protein product having a reduced quantity of the plurality of recombinant cell byproducts.

In various embodiments, wherein the composition comprising the recombinant protein and the plurality of recombinant cell byproducts and/or the protein product having a reduced quantity of the plurality of recombinant cell byproducts further undergoes an oxidation step.

In several embodiments, wherein the oxidization step comprises the addition of hydrogen peroxide.

In embodiments, wherein the ratio of the recombinant cell byproducts to recombinant protein in the composition comprising a recombinant protein and the plurality of recombinant cell byproducts is about 1:3 to about 3:1.

In some embodiments, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

In various embodiments, wherein less than about 10% of the weight of the protein product comprises recombinant cell byproducts.

In several embodiments, wherein less than about 5% of the weight of the protein product comprises recombinant cell byproducts.

In embodiments, wherein less than about 5%, less than about 1%, less than about 0.1%, or less than about 0.01% of the weight of the protein product comprises the off-flavor component.

In some embodiments, wherein the off-flavor component in the protein product is virtually undetectable to a standard consumer.

In various embodiments, wherein the EPS is generally inseparable from the recombinant protein when using size exclusion chromatography.

In several embodiments, wherein the EPS is naturally a component of a recombinant cell's cell wall.

In embodiments, wherein the EPS has an apparent size of about 13 kDa to about 27 kDa as characterized by a size exclusion chromatography column.

In some embodiments, wherein the EPS comprises mannose.

In various embodiments, wherein the EPS further comprises N-acetylglucosamine and/or glucose.

In several embodiments, wherein the EPS comprises about 91 mol % mannose, about 5 mol % N-acetylglucosamine, and about 3 mol % glucose as analyzed by gas chromatography in tandem with mass spectrometry.

In embodiments, wherein the EPS comprises an α(1,6)-linked backbone with α(1,2)-linked branches and/or α(1,3)-linked branches.

In some embodiments, wherein the EPS is a mannan.

In various embodiments, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

In several embodiments, wherein the recombinant cell type is selected from *Arxula* spp., *Arxula adeninivorans*,

*Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium* (*Talaromyces*) *emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

In embodiments, wherein the fungus is a *Pichia* species.

In some embodiments, wherein the *Pichia* species is *Komagataella phaffii* or *Komagataella pastoris*.

In various embodiments, wherein the recombinant protein is an enzyme, a nutritive protein, a food ingredient, or a food additive.

In several embodiments, wherein the enzyme is pepsinogen or pepsin.

In embodiments, wherein the protein is an egg-white protein.

In some embodiments, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

In various embodiments, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

In several embodiments, wherein the consumable composition comprising the protein product comprises food products, beverage products, or dietary supplements.

In embodiments, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

In some embodiments, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

In various embodiments, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

In several embodiments, wherein the processing the composition under conditions that separate the recombinant protein from the plurality of recombinant cell byproducts further comprises one or more of: one or more of: i) a cationic resin that reversibly attaches to the recombinant protein and does not substantially attach to the EPS, ii) an anionic resin that reversibly attaches to the recombinant protein and does not substantially attach to the EPS, iii) an enzyme that digests the recombinant protein or the EPS, and/or iv) a flocculant that attaches to the EPS and does not substantially attach to the recombinant protein.

In another aspect, the present disclosure provides a consumable composition obtained by any above-disclosed method.

In embodiments, after the adsorbent is reversibly attached to the recombinant cell byproduct, the adsorbent is separated from the fermentation media. In some cases, the adsorbent is separated with a strainer or other filtering apparatus. In various cases, the fermentation media is again supplemented with an adsorbent.

In another aspect, the present disclosure provides a consumable composition obtained by any above-disclosed method.

Flocculant-Based Purification

A further aspect of the present disclosure is a method for preparing a consumable composition. The method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an flocculant that reversibly attaches to one or more components of the plurality of recombinant cell byproducts and does not substantially attach to the recombinant protein; collecting the separated recombinant protein, thereby obtaining a protein product having a reduced quantity of the plurality of recombinant cell byproducts; and formulating a consumable composition comprising the protein product.

Figure 4:
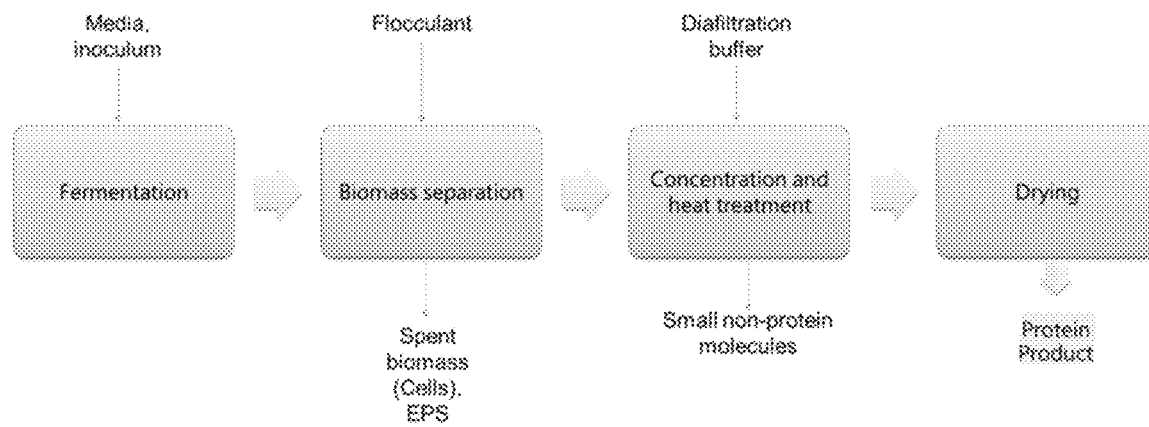

A illustrative method for producing a composition comprising a recombinant protein and a recombinant cell byproduct and separate the recombinant protein and the recombinant cell byproduct is shown in FIG. 4. The method of this aspect can be used to separate any extracellular product that is produced during a fermentation processes.

In embodiments, wherein the composition comprising the recombinant protein and the plurality of recombinant cell byproducts is a cell culturing medium.

In some embodiments, wherein the composition comprising the recombinant protein and the plurality of recombinant cell byproducts is a cell culture medium comprising recombinant cells that secreted the recombinant protein and the plurality of recombinant cell byproducts.

In various embodiments, wherein the composition comprising the recombinant protein and the plurality of recombinant cell byproducts has a pH greater than the isoelectric point (pI) of the recombinant protein.

In several embodiments, wherein the pH of the composition comprising the recombinant protein and the plurality of recombinant cell byproducts is not modified to achieve a pH greater than the pI of the recombinant protein.

In embodiments, wherein the flocculant is added to a culturing medium comprising recombinant cells that are secreting the recombinant protein and the plurality of recombinant cell byproducts.

In some embodiments, wherein once the flocculant attaches to one or more components of the plurality of recombinant cell byproducts, the flocculant is separated from the recombinant protein.

In various embodiments, wherein when the flocculant attaches to one or more components of the plurality of recombinant cell byproducts is isolated from the recombinant protein with a strainer, a filtering apparatus, and/or by centrifugation.

In several embodiments, the method further comprises supplementing the culturing medium again with a flocculant.

In embodiments, wherein the flocculant is provided to a biomass separation feed tank and to one or more components of the plurality of recombinant cell byproducts contemporaneously with removal of spent biomass including recombinant cells.

In some embodiments, wherein the flocculant is provided after removal of spent biomass including recombinant cells.

In various embodiments, wherein the composition comprising the recombinant protein and the plurality of recombinant cell byproducts lacks recombinant cells that secreted the recombinant protein and the plurality of recombinant cell byproducts.

In several embodiments, wherein the flocculant is an anionic flocculant or a neutral flocculant.

In embodiments, wherein the flocculant is Tramfloc 108, Tramfloc 109, Tramfloc 110, Tramfloc 111 or Tramfloc 120, Magnafloc 333, Magnafloc 355, or Gusmer Divergan, Dupont Polyox, Celite 545, Bentonite BE125, DIAION HPA25L, Chitosan 85% deacetylated, EZ DE, ultrapure diatomaceous earth, or Relisorb SP400.

In some embodiments, wherein the flocculant is provided in a column.

In various embodiments, wherein the processing the composition under conditions that separate the recombinant protein from the plurality of recombinant cell byproducts further comprises a chromatography system.

In several embodiments, wherein the chromatography system operates in batch mode with an axial flow column or a radial flow column or a centrifugal column or by use of a membrane chromatography column or the chromatography system operates in a continuous mode comprising multiple columns in parallel, with the feed to the columns being switchable such that various steps in a chromatography process (e.g., equilibration, load, elute, and clean), occur contemporaneously.

In embodiments, wherein the continuous mode comprises a simulated moving bed (SMB) or an Ion Separator (e.g., ISEP®) system.

In some embodiments, wherein the composition comprising the recombinant protein and the plurality of recombinant cell byproducts was previously treated to remove spent biomass including recombinant cells and/or was previously treated to remove small non-protein molecules.

In various embodiments, wherein the treatment to remove small non-protein molecules comprises a step that concentrates the composition comprising the recombinant protein and the plurality of recombinant cell byproducts.

In several embodiments, wherein the treatment to remove small non-protein molecules comprises a diafiltration buffer.

In embodiments, the method further comprises a concentration step and/or dia-filtration treatment of the separated recombinant protein to produce a protein-containing composition having a preferred pH and/or ionic condition.

In some embodiments, wherein the protein-containing composition having a preferred pH and/or ionic condition is further heat treated and/or dried.

In various embodiments, wherein the composition comprising the recombinant protein and the plurality of recombinant cell byproducts and/or the protein product having a reduced quantity of the plurality of recombinant cell byproducts is further heat treated and/or dried.

In several embodiments, wherein the heat treatment separates the recombinant protein and the off-flavor component, wherein the heat is applied at a temperature and duration such that the off-flavor component is volatized and a gaseous off-flavor component is removable.

In embodiments, wherein a vacuum is applied contemporaneous with the application of heat and the vacuum facilitates removal of the gaseous off-flavor component.

In some embodiments, wherein the off-flavor component is an acid, an alcohol, an aldehyde, an aromatic, an ester, or a ketone.

In various embodiments, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

In several embodiments, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

In embodiments, wherein the method comprises agitation during the heat treatment.

In some embodiments, wherein the heat treatment and/or drying step produces a dry protein product having a reduced quantity of the plurality of recombinant cell byproducts.

In various embodiments, wherein the composition comprising the recombinant protein and the plurality of recombinant cell byproducts and/or the protein product having a reduced quantity of the plurality of recombinant cell byproducts further undergoes an oxidation step In several embodiments, wherein the oxidization step comprises the addition of hydrogen peroxide.

In embodiments, wherein the ratio of the recombinant cell byproducts to recombinant protein in the composition comprising a recombinant protein and the plurality of recombinant cell byproducts is about 1:3 to about 3:1.

In some embodiments, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

In various embodiments, wherein less than about 10% of the weight of the protein product comprises recombinant cell byproducts.

In several embodiments, wherein less than about 5% of the weight of the protein product comprises recombinant cell byproducts.

In embodiments, wherein less than about 5%, less than about 1%, less than about 0.1%, or less than about 0.01% of the weight of the protein product comprises the off-flavor component.

In some embodiments, wherein the off-flavor component in the protein product is virtually undetectable to a standard consumer.

In various embodiments, wherein the EPS is generally inseparable from the recombinant protein when using size exclusion chromatography.

In several embodiments, wherein the EPS is naturally a component of a recombinant cell's cell wall.

In embodiments, wherein the EPS has an apparent size of about 13 kDa to about 27 kDa as characterized by a size exclusion chromatography column.

In some embodiments, wherein the EPS comprises mannose.

In various embodiments, wherein the EPS further comprises N-acetylglucosamine and/or glucose.

In several embodiments, wherein the EPS comprises about 91 mol % mannose, about 5 mol % N-acetylglucosamine, and about 3 mol % glucose as analyzed by gas chromatography in tandem with mass spectrometry.

In embodiments, wherein the EPS comprises an α(1,6)-linked backbone with α(1,2)-linked branches and/or α(1,3)-linked branches.

In some embodiments, wherein the EPS is a mannan.

In various embodiments, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

In several embodiments, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium* (*Talaromyces*) *emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

In embodiments, wherein the fungus is a *Pichia* species.

In some embodiments, wherein the *Pichia* species is *Komagataella phaffii* or *Komagataella pastoris*.

In various embodiments, wherein the recombinant protein is an enzyme, a nutritive protein, a food ingredient, or a food additive.

In several embodiments, wherein the enzyme is pepsinogen or pepsin.

In embodiments, wherein the protein is an egg-white protein.

In some embodiments, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

In various embodiments, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guinea-fowl, pheasant, or emu.

In several embodiments, wherein the consumable composition comprising the protein product comprises food products, beverage products, or dietary supplements.

In embodiments, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

In some embodiments, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

In various embodiments, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

In several embodiments, wherein the processing the composition under conditions that separate the recombinant protein from the plurality of recombinant cell byproducts further comprises one or more of: i) a cationic resin that reversibly attaches to the recombinant protein and does not substantially attach to the EPS, ii) an anionic resin that reversibly attaches to the recombinant protein and does not substantially attach to the EPS, iii) an enzyme that digests the recombinant protein or the EPS, and/or iv) an adsorbent that attaches to the EPS and does not substantially attach to the recombinant protein.

In another aspect, the present disclosure provides a consumable composition obtained by any above-disclosed method.

Protein Products and Protein-Containing Consumable Compositions

Another aspect of the present disclosure is a protein product prepared by any herein-disclosed method.

Yet another aspect of the present disclosure is a consumable composition comprising any-herein disclosed protein product.

In an aspect, the present disclosure provides a herein-disclosed consumable composition of for use in a food product.

In embodiments, the consumable composition further includes at least one consumable ingredient. In some cases, the consumable ingredient is a solvent, e.g., water, carbonated water, alcohol, juice, and any other commercially available drink.

In embodiments, the consumable composition comprising the protein product and having a reduced quantity of the recombinant cell byproduct has one or more different properties relative to an equivalent consumable composition that does not have a reduced quantity of the recombinant cell byproduct.

In embodiments, the properties include density, viscosity, gel hardness, chewiness, foam capacity, foam stability, solubility, clarity, texture, foaming, whipping, seeping, gelling, clarification, coagulation, coating, crystallization control, drying, edible packaging film, finishing, flavor, fortification, freezability, gloss, humectancy, insulation, moisturizing, mouthfeel, pH stability, protein enrichment, richness, shelf life extension, structure, tenderization, texture, thickening, water-binding, oil-binding, browning, emulsification, nitrogen:carbon ratio and/or anti-microbial activity. In some cases, the different property comprises a desirable increase in the property or the different property comprises a desirable decrease in the property.

An aspect of the present disclosure is a method for preparing a consumable composition. The method comprising steps of: obtaining a composition comprising a recombinant protein and a recombinant cell byproduct, wherein the recombinant cell byproduct is an exopolysaccharide (EPS) or an off-flavor component; processing the composition under conditions that separate the recombinant protein and the EPS or off-flavor component; collecting the separated recombinant protein, thereby obtaining a protein product having a reduced quantity of the EPS and/or collecting the separated EPS, thereby obtaining an EPS product having a reduced quantity of the recombinant protein; and formulating a consumable composition comprising the protein product or the EPS product. In this method the processing step comprises: i) a resin that reversibly attaches to the recombinant protein and does not substantially attach to the EPS, ii) an enzyme that digests the recombinant protein or the EPS, iii) an absorbent that reversibly attaches to the EPS and does not substantially attach to the recombinant protein, and/or iv) a flocculant that attaches to the EPS and does not substantially attach to the recombinant protein.

Method for Collecting a Recombinant Cell Byproduct

In any of the herein-disclosed aspects or embodiments, a method may further comprise a step of collecting the separated recombinant cell byproduct. In some cases, the method further comprises a step of concentrating and/or purifying the separated recombinant cell byproduct, thereby obtaining an EPS product having a reduced quantity of the recombinant protein.

Figure 5:
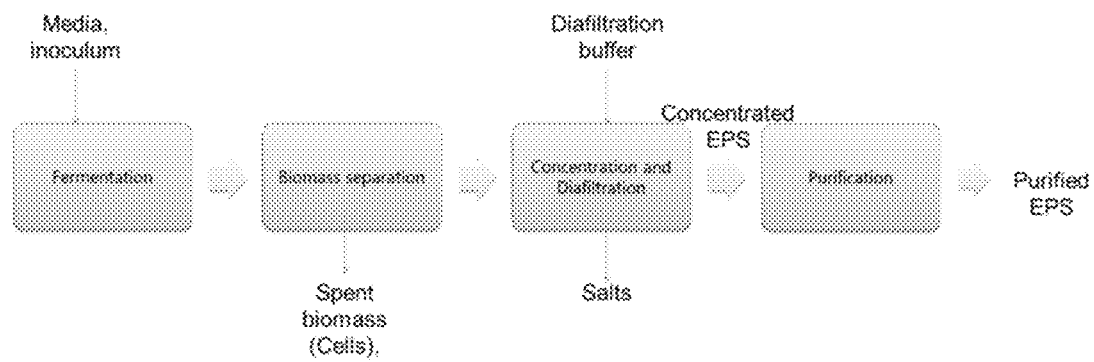

A illustrative method for producing a composition comprising a recombinant protein and a recombinant cell byproduct and separate the recombinant protein and the recombinant cell byproduct is shown in FIG. 5. The method of this aspect can be used to collect any extracellular product that is produced during a fermentation processes.

In an aspect, the present disclosure provides an exopolysaccharide (EPS) product produced by any herein-disclosed method.

In another aspect, the present disclosure provides a consumable composition comprising any herein-disclosed exopolysaccharide (EPS) product.

In embodiments, the consumable composition further includes at least one consumable ingredient.

In some embodiments, the consumable composition is for use as a food product.

In various embodiments, the EPS provides nutritional supplementation to a consumer.

In embodiments, the EPS improves gastrointestinal health to a consumer by preventing binding of pathogens to a consumer's digestive tract cell.

In some embodiments, the EPS improves gastrointestinal health to a consumer by promoting a favorable gut microbiome.

An aspect of the present disclosure is a method for preparing a consumable composition. The method comprising steps of: obtaining a composition comprising a recombinant protein and a recombinant cell byproduct, wherein the recombinant cell byproduct is an exopolysaccharide (EPS); processing the composition under conditions that separate the recombinant protein and the EPS; collecting the separated recombinant protein, thereby obtaining a protein product having a reduced quantity of the EPS and/or collecting the separated EPS, thereby obtaining an EPS product having a reduced quantity of the recombinant protein; and formulating a consumable composition comprising the protein product or the EPS product. In this method the processing step comprises: i) a resin that reversibly attaches to the recombinant protein and does not substantially attach to the EPS, ii) an enzyme that digests the recombinant protein or the EPS, iii) an absorbent that reversibly attaches to the EPS and does not substantially attach to the recombinant protein, and/or iv) a flocculant that attaches to the EPS and does not substantially attach to the recombinant protein.

Features of Methods of the Present Disclosure

In embodiments, the ratio of recombinant cell byproduct to recombinant protein in the composition comprising a recombinant protein and a recombinant cell byproduct is about 1:3 to about 3:1. In some cases, the ratio is about 1:1.

In some embodiments, the protein product having a reduced quantity of the recombinant cell byproduct comprises an at least 50% reduction in recombinant cell byproduct quantity relative to the composition comprising a recombinant protein and a recombinant cell byproduct. In some cases, the protein product has an at least 75% reduction, at least 80% reduction, at least 90% reduction, or at least 95% reduction in recombinant cell byproduct quantity relative to the composition comprising a recombinant protein and a recombinant cell byproduct.

In various embodiments, less than about 10% of the weight of the protein product comprises the recombinant cell byproduct. In some cases, less than about 5% of the weight of the protein product comprises the recombinant cell byproduct.

In embodiments, the EPS or off-flavor component is generally inseparable from the recombinant protein when using size exclusion chromatography.

In some embodiments, the EPS or off-flavor component is naturally a component of a recombinant cell's cell wall. In some cases, the EPS or off-flavor component present in the composition comprising the recombinant protein and the recombinant cell byproduct was secreted from the recombinant cell rather than being incorporated into the recombinant cell's cell wall.

In various embodiments, the EPS has an apparent size of about 13 kDa to about 27 kDa as characterized by a size exclusion chromatography column.

In embodiments, the EPS comprises mannose. In some cases, the EPS further comprises N-acetylglucosamine and/or glucose.

In some embodiments, the EPS comprises about 91 mol % mannose, about 5 mol % N-acetylglucosamine, and about 3 mol % glucose as analyzed by gas chromatography in tandem with mass spectrometry. EPS can be quantified using a method using a pb binding column. An analytical Hyper-REZ XP Pb++ column (8 um, 300×7.7 mm, Thermofisher Sci.) can be used for the measurement, which is eluted with water on UltiMate 3000 system (Thermofisher Sci.) operated at a flow rate of 0.6 mL/min and monitored with a refractive index detector.

In various embodiments, the EPS comprises an α(1,6)-linked backbone with α(1,2)-linked branches and/or α(1,3)-linked branches.

In embodiments, the EPS is a mannan.

In some embodiments, the recombinant cell is cell that expresses and/or secretes EPS and is selected from a fungal cell, such as filamentous fungus or a yeast, a bacterial cell, a plant cell, an insect cell, or a mammalian cell.

In various embodiments, the recombinant cell type is selected from *Arxula* spp., *Arxula* adeninivorans, *Kluyveromyces* spp., *Kluyveromyces lactis, Komagataella phaffii, Pichia* spp., *Pichia angusta, Pichia pastoris, Saccharomyces* spp., *Saccharomyces cerevisiae, Schizosaccharomyces* spp., *Schizosaccharomyces pombe, Yarrowia* spp., *Yarrowia lipolytica, Agaricus* spp., *Agaricus bisporus, Aspergillus* spp., *Aspergillus awamori, Aspergillus fumigatus, Aspergillus nidulans, Aspergillus niger, Aspergillus oryzae, Bacillus subtilis, Colletotrichum* spp., *Colletotrichum gloeosporiodes, Endothia* spp., *Endothia parasitica, Escherichia coli, Fusarium* spp., *Fusarium graminearum, Fusarium solani, Mucor* spp., *Mucor miehei, Mucor pusillus, Myceliophthora* spp., *Myceliophthora thermophila, Neurospora* spp., *Neurospora crassa, Penicillium* spp., *Penicillium camemberti, Penicillium canescens, Penicillium chrysogenum, Penicillium (Talaromyces) emersonii, Penicillium funiculo sum, Penicillium purpurogenum, Penicillium roqueforti, Pleurotus* spp., *Pleurotus ostreatus, Pseudomonas* spp., *Rhizomucor* spp., *Rhizomucor miehei, Rhizomucor pusillus, Rhizopus* spp., *Rhizopus arrhizus, Rhizopus oligosporus, Rhizopus oryzae, Trichoderma* spp., *Trichoderma altroviride, Trichoderma reesei*, and *Trichoderma vireus*. In some cases, the fungus is a *Pichia* species. In some cases, the *Pichia* species is *Komagataella phaffii* or *Komagataella pastoris*.

In embodiments, the recombinant protein is an enzyme, a nutritive protein, a food ingredient, or a food additive. In some cases, the enzyme is pepsinogen or pepsin.

In some embodiments, the protein is an egg-white protein. Eggs are almost an essential food component across the world. There is a huge market for eggs and egg ingredients. Eggs provide high protein and nutraceutical content and have been looked at as complete food in combination with milk. However, the eggs have a limited shelf life and are prone to bringing in infectious pathogens. People around the world specifically kids have been diagnosed with food allergies or have dietary restrictions inhibiting them to consume eggs. Also, to improve the productivity of the industrial scale production of eggs has a introduced use of growth hormones in addition to inhumane conditions for culturing chicken. The current egg substitutes have major limitations. None of the products extend the application to foaming as well as gelation. The product compositions in the package are unstable over time.

In some cases, the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof. In various cases, the egg-white protein is OVA, OVD, OVT, or OVL. In some cases, an egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

Any composition or method disclosed herein is applicable to any herein-disclosed composition or method. In other words, any aspect or embodiment described herein can be combined with any other aspect or embodiment as disclosed herein.

Definitions

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Sequence identity, such as for the purpose of assessing percent complementarity, may be measured by any suitable alignment algorithm, including but not limited to the Needleman-Wunsch algorithm (see e.g., the EMBOSS Needle aligner available at the World Wide Web at ebi.ac.uk/Tools/psa/emboss needle/nucleotide.html, optionally with default settings), the BLAST algorithm (see e.g., the BLAST alignment tool available at blast.ncbi.nlm.nih.gov/Blast.cgi, optionally with default settings), and the Smith-Waterman algorithm (see e.g., the EMBOSS Water aligner available at the World Wide Web at ebi.ac.uk/Tools/psa/emboss water/nucleotide.html, optionally with default settings). Optimal alignment may be assessed using any suitable parameters of a chosen algorithm, including default parameters.

The term "bird" includes both domesticated birds and non-domesticated birds such as wildlife and the like. Birds include, but are not limited to, poultry, fowl, waterfowl, game bird, ratite (e.g., flightless bird), chicken (*Gallus gallus domesticus*), quail, turkey, duck, ostrich (*Struthio camelus*), Somali ostrich (*Struthio molybdophanes*), goose, gull, guineafowl, pheasant, emu (*Dromaius novaehollandiae*), American *Rhea* (*Rhea americana*), Darwin's *Rhea* (*Rhea pennata*), and kiwi. Tissues, cells, and their progeny of a biological entity obtained in vivo or cultured in vitro are also encompassed. A bird may lay eggs.

As used herein, the terms "consumable composition" or "consumable product" refers to a composition or product, which comprises a recombinant protein or composition comprising recombinant protein and other ingredients and may be consumed (e.g., by eating, chewing, drinking, tasting, ingesting, or swallowing). Consumable products include food products, beverage products, dietary supplements, food additives, pharmaceutical products, and hygiene products, as non-limiting examples. Food products include, but are not limited to, baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings. Beverage products include, but are not limited to, soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks. Dietary supplements include multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement. A consumer of a consumable product or consumable composition is any animal, including domesticated animals (e.g., livestock) and humans.

Processing of a consumable product to form a processed consumable product may include, but is not limited to, freezing, chilling, heating, baking, roasting, broiling, boiling, blanching, packaging, canning, bleaching, enriching, drying, pressing, grinding, mixing, parcooking, cooking, proofing, marinating, cutting, slicing, dicing, crushing, shredding, chopping, shaking, coring, spiralizing, rolling, juicing, straining, filtering, kneading, whisking, beating, whipping, grating, stuffing, peeling, deseeding, smoking, curing, salting, preserving, pickling, fermenting, homogenizing, pasteurizing, sterilizing, stabilizing, blending, pureeing, fortifying, refining, hydrogenating, aging, extending shelf life, or adding enzymes.

As used herein, the term "solvent" refers to a liquid, which may be mixed with or used to dissolve a composition or one or more components of a composition such as a protein. Non-limiting examples of a solvent include water, ethanol, and isopropanol. The solvent can be potable. The solvent can be water. Non-limiting examples of water include purified water, distilled water, double distilled water, deionized water, distilled deionized water, drinking water, well water, tap water, spring water, bottled water, carbonated water, mineral water, flavored water, or any combination thereof. A solvent may be a combination of two or more distinct solvents.

Additional Embodiments

Embodiment 1. A method for preparing a consumable composition, the method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an anionic resin that reversibly attaches to the recombinant protein and does not substantially attach to the plurality of recombinant cell byproducts; collecting the separated recombinant protein, thereby obtaining a protein product having a reduced quantity of the plurality of recombinant cell byproducts; and formulating a consumable composition comprising the protein product.

Embodiment 2. The method of Embodiment 1, wherein the composition comprising the recombinant protein and the plurality of recombinant cell byproducts is a cell culturing medium.

Embodiment 3. The method of Embodiment 1 or Embodiment 2, wherein the composition comprising the recombinant protein and the plurality of recombinant cell byproducts is a cell culture medium comprising recombinant cells that secreted the recombinant protein and the plurality of recombinant cell byproducts.

Embodiment 4. The method of Embodiment 1, wherein the composition comprising the recombinant protein and the plurality of recombinant cell byproducts lacks recombinant cells that secreted the recombinant protein and the plurality of recombinant cell byproducts.

Embodiment 5. The method of any one of Embodiments 1 to 4, wherein the composition comprising the recombinant protein and the plurality of recombinant cell byproducts has a pH greater than the isoelectric point (pI) of the recombinant protein.

Embodiment 6. The method of Embodiment 5, wherein the pH of the composition comprising the recombinant protein and the plurality of recombinant cell byproducts is not modified to achieve a pH greater than the pI of the recombinant protein.

Embodiment 7. The method of any one of Embodiments 1 to 6, wherein the anion resin is a strong anion exchange resin or a weak anion exchange resin.

Embodiment 8. The method of any one of Embodiments 1 to 7, wherein the anion resin is one or more of Capto Q resin, a DEAE type weak anion exchanger, a resin with trimethyl aminoethyl groups, a resin with triethyl aminoethyl groups, a resin with quaternary amine groups.

Embodiment 9. The method of any one of Embodiments 1 to 8, wherein the anion resin is a component of a chromatography system.

Embodiment 10. The method of Embodiment 9, wherein the chromatography system operates in batch mode with an axial flow column or a radial flow column or a centrifugal column or by use of a membrane chromatography column.

Embodiment 11. The method of Embodiment 9, wherein the chromatography system operates in a continuous mode comprising multiple columns in parallel, with the feed to the columns being switchable such that various steps in a chromatography process (e.g., equilibration, load, elute, and clean), occur contemporaneously.

Embodiment 12. The method of Embodiment 11, wherein the continuous mode comprises a simulated moving bed (SMB) or an Ion Separator (e.g., ISEP®) system.

Embodiment 13. The method of any one of Embodiments 4 to 12, wherein the composition comprising the recombinant protein and the plurality of recombinant cell byproducts was previously treated to remove spent biomass including recombinant cells and/or was previously treated to remove small non-protein molecules.

Embodiment 14. The method of Embodiment 13, wherein the treatment to remove small non-protein molecules comprises a step that concentrates the composition comprising the recombinant protein and the plurality of recombinant cell byproducts.

Embodiment 15. The method of Embodiment 13 or Embodiment 14, wherein the treatment to remove small non-protein molecules comprises a diafiltration buffer.

Embodiment 16. The method of any one of Embodiments 1 to 15 further comprising a concentration step and/or diafiltration treatment of the separated recombinant protein to produce a protein-containing composition having a preferred pH and/or ionic condition.

Embodiment 17. The method of Embodiment 16, wherein the protein-containing composition having a preferred pH and/or ionic condition is further heat treated and/or dried.

Embodiment 18. The method of any one of Embodiments 1 to 15, wherein the composition comprising the recombinant protein and the plurality of recombinant cell byproducts and/or the protein product having a reduced quantity of the plurality of recombinant cell byproducts is further heat treated and/or dried.

Embodiment 19. The method of Embodiment 17 or Embodiment 18, wherein the heat treatment separates the recombinant protein and the off-flavor component, wherein the heat is applied at a temperature and duration such that the off-flavor component is volatized and a gaseous off-flavor component is removable.

Embodiment 20. The method of Embodiment 19, wherein a vacuum is applied contemporaneous with the application of heat and the vacuum facilitates removal of the gaseous off-flavor component.

Embodiment 21. The method of any one of Embodiments 1 to 20, wherein the off-flavor component is an acid, an alcohol, an aldehyde, an aromatic, an ester, or a ketone.

Embodiment 22. The method of any one of Embodiments 1 to 21, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

Embodiment 23. The method of any one of Embodiments 17 to 22, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

Embodiment 24. The method any one of Embodiments 17 to 23, wherein the method comprises agitation during the heat treatment.

Embodiment 25. The method any one of Embodiments 17 to 24, wherein the heat treatment and/or drying step produces a dry protein product having a reduced quantity of the plurality of recombinant cell byproducts.

Embodiment 26. The method of any one of Embodiments 1 to 25, wherein the composition comprising the recombinant protein and the plurality of recombinant cell byproducts and/or the protein product having a reduced quantity of the plurality of recombinant cell byproducts further undergoes an oxidation step, e.g., comprising the addition of hydrogen peroxide.

Embodiment 27. The method of any one of Embodiments 1 to 26, wherein the ratio of the recombinant cell byproducts to recombinant protein in the composition comprising a recombinant protein and the plurality of recombinant cell byproducts is about 1:3 to about 3:1.

Embodiment 28. The method of Embodiment 27, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

Embodiment 29. The method of Embodiment 28, wherein less than about 10% of the weight of the protein product comprises recombinant cell byproducts.

Embodiment 30. The method of any one of Embodiments 1 to 29, wherein less than about 5% of the weight of the protein product comprises recombinant cell byproducts.

Embodiment 31. The method of any one of Embodiments 1 to 30, wherein less than about 5%, less than about 1%, less than about 0.1%, or less than about 0.01% of the weight of the protein product comprises the off-flavor component.

Embodiment 32. The method of any one of Embodiments 1 to 31, wherein the off-flavor component in the protein product is virtually undetectable to a standard consumer.

Embodiment 33. The method of any one of Embodiments 1 to 32, wherein the EPS is generally inseparable from the recombinant protein when using size exclusion chromatography.

Embodiment 34. The method of any one of Embodiments 1 to 33, wherein the EPS is naturally a component of a recombinant cell's cell wall.

Embodiment 35. The method of one of Embodiments 1 to 34, wherein the EPS has an apparent size of about 13 kDa to about 27 kDa as characterized by a size exclusion chromatography column.

Embodiment 36. The method of any one of Embodiments 1 to 35, wherein the EPS comprises mannose.

Embodiment 37. The method of any one of Embodiments 1 to 36, wherein the EPS further comprises N-acetylglucosamine and/or glucose.

Embodiment 38. The method of any one of Embodiments 1 to 37, wherein the EPS comprises about 91 mol % mannose, about 5 mol % N-acetylglucosamine, and about 3 mol % glucose as analyzed by gas chromatography in tandem with mass spectrometry.

Embodiment 39. The method of any one of Embodiments 1 to 38, wherein the EPS comprises an $\alpha(1,6)$-linked backbone with $\alpha(1,2)$-linked branches and/or $\alpha(1,3)$-linked branches.

Embodiment 40. The method of any one of Embodiments 1 to 39, wherein the EPS is a mannan.

Embodiment 41. The method of any one of Embodiments 1 to 40, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

Embodiment 42. The method of any one of Embodiments 1 to 41, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicil-*

*lium canescens, Penicillium chrysogenum, Penicillium (Talaromyces) emersonii, Penicillium funiculo sum, Penicillium purpurogenum, Penicillium roqueforti, Pleurotus* spp., *Pleurotus ostreatus, Pseudomonas* spp., *Rhizomucor* spp., *Rhizomucor miehei, Rhizomucor pusillus, Rhizopus* spp., *Rhizopus arrhizus, Rhizopus oligosporus, Rhizopus oryzae, Trichoderma* spp., *Trichoderma altroviride, Trichoderma reesei*, and *Trichoderma vireus*.

Embodiment 43. The method of Embodiment 41 or Embodiment 42, wherein the fungus is a *Pichia* species.

Embodiment 44. The method of Embodiment 43, wherein the *Pichia* species is *Komagataella phaffii* or *Komagataella pastoris*.

Embodiment 45. The method of any one of Embodiments 1 to 44, wherein the recombinant protein is an enzyme, a nutritive protein, a food ingredient, or a food additive.

Embodiment 46. The method of Embodiment 45, wherein the enzyme is pepsinogen or pepsin.

Embodiment 47. The method of Embodiment 45, wherein the protein is an egg-white protein.

Embodiment 48. The method of Embodiment 47, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

Embodiment 49. The method of Embodiment 47 or Embodiment 48, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

Embodiment 50. The method of any one of Embodiments 1 to 49, wherein the consumable composition comprising the protein product comprises food products, beverage products, or dietary supplements.

Embodiment 51. The method of Embodiment 50, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

Embodiment 52. The method of Embodiment 50, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

Embodiment 53. The method of Embodiment 50, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

Embodiment 54. The method of any one of Embodiments 1 to 53, wherein the processing the composition under conditions that separate the recombinant protein from the plurality of recombinant cell byproducts further comprises one or more of: i) one or more cation exchange resin that reversibly attach to the recombinant protein and does not substantially attach to the EPS, ii) an enzyme that digests the recombinant protein or the EPS, iii) an adsorbent that reversibly attaches to the EPS and does not substantially attach to the recombinant protein, and/or iv) a flocculant that attaches to the EPS and does not substantially attach to the recombinant protein.

Embodiment 55. A consumable composition obtained by the method of any one of Embodiments 1 to 54.

Embodiment 56. A method for preparing a consumable composition, the method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises one or more cation exchange resins that reversibly attach to the recombinant protein and do not substantially attach to the plurality of recombinant cell byproducts; collecting the separated recombinant protein, thereby obtaining a protein product having a reduced quantity of the plurality of recombinant cell byproducts; and formulating a consumable composition comprising the protein product.

Embodiment 57. The method of Embodiment 56, wherein the one or more cation exchange resins comprise a strong cation exchange resin, e.g., a sulfopropyl-, sulfomethyl-, or sulphonate-type resin, and/or a weak cation exchange resin, e.g., a carboxymethyl-type resin.

Embodiment 58. The method of Embodiment 56 or Embodiment 57, wherein the one or more cation exchange resins comprise poly styrene divinyl benzene, poly methacrylate or cellulose or cross-linked dextran or cross-linked agarose or inorganic materials coated with hydrophilic polymers.

Embodiment 59. The method of any one of Embodiments 56 to 58, wherein the one or more cation exchange resins have a particle size of from about 50 μm and about 200 μm and/or have a protein binding capacity of from about 50 to about 100 g protein/L resin.

Embodiment 60. The method of any one of Embodiments 56 to 59, wherein the one or more cation exchange resins comprise Cytiva Capto S, HP20, resindion SP400, Sepragen S, SP20, and/or Mitsubishi Relisorb EXE349.

Embodiment 61. The method of any one of Embodiments 56 to 60, wherein the processing step comprises two cationic resins, wherein the two cationic resins are in a ratio of 1:5 to 5:1, 1:4 to 4:1, 1:3 to 3:1, 1:2 to 2:1, or 1:1.

Embodiment 62. The method of Embodiment 61, wherein the two resins are SP400 and Sepragen S and in a ratio of about 3:1, e.g., 2.75:1.25.

Embodiment 63. The method of any one of Embodiments 56 to 62, wherein the composition comprising the recombinant protein and the plurality of recombinant cell byproducts lacks recombinant cells that secreted the recombinant protein and the plurality of recombinant cell byproducts.

Embodiment 64. The method of any one of Embodiments 56 to 63, wherein the composition comprising the recombinant protein and the plurality of recombinant cell byproducts has a pH less than the isoelectric point (pI) of the recombinant protein, which is achieved by lowering the pH of the composition comprising the recombinant protein and the plurality of recombinant cell byproducts.

Embodiment 65. The method of any one of Embodiments 56 to 64, wherein the one or more cationic resins are components of a chromatography system, wherein the chromatography system operates in batch mode with an axial flow column or a radial flow column or a centrifugal column or by use of a membrane chromatography column.

Embodiment 66. The method of any one of Embodiments 56 to 64, wherein the one or more cationic resins are components of a chromatography system, wherein the chromatography system operates in a continuous mode comprising multiple columns in parallel, with the feed to the columns being switchable such that various steps in a chromatography process (e.g., equilibration, load, elute, and clean), occur contemporaneously.

Embodiment 67. The method of Embodiment 66, wherein the continuous mode comprises a simulated moving bed (SMB) or an Ion Separator (e.g., ISEP®) system.

Embodiment 68. The method of any one of Embodiments 62 to 67, wherein the composition comprising the recombinant protein and the plurality of recombinant cell byproducts was previously treated to remove spent biomass including recombinant cells and/or was previously treated to remove small non-protein molecules.

Embodiment 69. The method of Embodiment 68, wherein the treatment to remove small non-protein molecules comprises a step that concentrates the composition comprising the recombinant protein and the plurality of recombinant cell byproducts.

Embodiment 70. The method of Embodiment 68 or Embodiment 69, wherein the treatment to remove small non-protein molecules comprises a diafiltration buffer.

Embodiment 71. The method of any one of Embodiments 56 to 70 further comprising a concentration step and/or diafiltration treatment of the separated recombinant protein to produce a protein-containing composition having a preferred pH and/or ionic condition.

Embodiment 72. The method of Embodiment 71, wherein the protein-containing composition having a preferred pH and/or ionic condition is further heat treated and/or dried.

Embodiment 73. The method of any one of Embodiments 56 to 70, wherein the composition comprising the recombinant protein and the plurality of recombinant cell byproducts and/or the protein product having a reduced quantity of the plurality of recombinant cell byproducts is further heat treated and/or dried.

Embodiment 74. The method of Embodiment 72 or Embodiment 73, wherein the heat treatment separates the recombinant protein and the off-flavor component, wherein the heat is applied at a temperature and duration such that the off-flavor component is volatized and a gaseous off-flavor component is removable.

Embodiment 75. The method of Embodiment 74, wherein a vacuum is applied contemporaneous with the application of heat and the vacuum facilitates removal of the gaseous off-flavor component.

Embodiment 76. The method of any one of Embodiments 56 to 75, wherein the off-flavor component is an acid, an alcohol, an aldehyde, an aromatic, an ester, or a ketone.

Embodiment 77. The method of any one of Embodiments 56 to 76, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

Embodiment 78. The method of any one of Embodiments 72 to 77, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

Embodiment 79. The method any one of Embodiments 72 to 78, wherein the method comprises agitation during the heat treatment.

Embodiment 80. The method any one of Embodiments 72 to 79, wherein the heat treatment and/or drying step produces a dry protein product having a reduced quantity of the plurality of recombinant cell byproducts.

Embodiment 81. The method of any one of Embodiments 56 to 80, wherein the composition comprising the recombinant protein and the plurality of recombinant cell byproducts and/or the protein product having a reduced quantity of the plurality of recombinant cell byproducts further undergoes an oxidation step, e.g., comprising the addition of hydrogen peroxide.

Embodiment 82. The method of any one of Embodiments 56 to 81, wherein the ratio of the recombinant cell byproducts to recombinant protein in the composition comprising a recombinant protein and the plurality of recombinant cell byproducts is about 1:3 to about 3:1.

Embodiment 83. The method of Embodiment 82, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

Embodiment 84. The method of Embodiment 83, wherein less than about 10% of the weight of the protein product comprises recombinant cell byproducts.

Embodiment 85. The method of any one of Embodiments 56 to 84, wherein less than about 5% of the weight of the protein product comprises recombinant cell byproducts.

Embodiment 86. The method of any one of Embodiments 56 to 85, wherein less than about 5%, less than about 1%, less than about 0.1%, or less than about 0.01% of the weight of the protein product comprises the off-flavor component.

Embodiment 87. The method of any one of Embodiments 56 to 86, wherein the off-flavor component in the protein product is virtually undetectable to a standard consumer.

Embodiment 88. The method of any one of Embodiments 56 to 87, wherein the EPS is generally inseparable from the recombinant protein when using size exclusion chromatography.

Embodiment 89. The method of any one of Embodiments 56 to 88, wherein the EPS is naturally a component of a recombinant cell's cell wall.

Embodiment 90. The method of one of Embodiments 56 to 89, wherein the EPS has an apparent size of about 13 kDa to about 27 kDa as characterized by a size exclusion chromatography column.

Embodiment 91. The method of any one of Embodiments 56 to 90, wherein the EPS comprises mannose.

Embodiment 92. The method of any one of Embodiments 56 to 91, wherein the EPS further comprises N-acetylglucosamine and/or glucose.

Embodiment 93. The method of any one of Embodiments 56 to 92, wherein the EPS comprises about 91 mol % mannose, about 5 mol % N-acetylglucosamine, and about 3 mol % glucose as analyzed by gas chromatography in tandem with mass spectrometry.

Embodiment 94. The method of any one of Embodiments 56 to 93, wherein the EPS comprises an α(1,6)-linked backbone with α(1,2)-linked branches and/or α(1,3)-linked branches.

Embodiment 95. The method of any one of Embodiments 56 to 94, wherein the EPS is a mannan.

Embodiment 96. The method of any one of Embodiments 56 to 95, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

Embodiment 97. The method of any one of Embodiments 56 to 96, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium* (*Talaromyces*) *emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

Embodiment 98. The method of Embodiment 96 or Embodiment 97, wherein the fungus is a *Pichia* species.

Embodiment 99. The method of Embodiment 98, wherein the *Pichia* species is *Komagataella phaffii* or *Komagataella pastoris*.

Embodiment 100. The method of any one of Embodiments 56 to 99, wherein the recombinant protein is an enzyme, a nutritive protein, a food ingredient, or a food additive.

Embodiment 101. The method of Embodiment 100, wherein the enzyme is pepsinogen or pepsin.

Embodiment 102. The method of Embodiment 100, wherein the protein is an egg-white protein.

Embodiment 103. The method of Embodiment 102, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

Embodiment 104. The method of Embodiment 102 or Embodiment 103, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

Embodiment 105. The method of any one of Embodiments 56 to 104, wherein the consumable composition comprising the protein product comprises food products, beverage products, or dietary supplements.

Embodiment 106. The method of Embodiment 105, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

Embodiment 107. The method of Embodiment 105, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

Embodiment 108. The method of Embodiment 105, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

Embodiment 109. The method of any one of Embodiments 56 to 108, wherein the processing the composition under conditions that separate the recombinant protein from the plurality of recombinant cell byproducts further comprises one or more of: i) an anionic resin that reversibly attaches to the recombinant protein and does not substantially attach to the EPS, ii) an enzyme that digests the recombinant protein or the EPS, iii) an adsorbent that reversibly attaches to the EPS and does not substantially attach to the recombinant protein, and/or iv) a flocculant that attaches to the EPS and does not substantially attach to the recombinant protein.

Embodiment 110. A consumable composition obtained by the method of any one of Embodiments 56 to 109.

Embodiment 111. A method for preparing a consumable composition, the method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises a flocculant that reversibly attaches to one or more components of the plurality of recombinant cell byproducts and does not substantially attach to the recombinant protein; collecting the separated recombinant protein, thereby obtaining a protein product having a reduced quantity of the plurality of recombinant cell byproducts; and formulating a consumable composition comprising the protein product.

Embodiment 112. The method of Embodiment 111, wherein the composition comprising the recombinant protein and the plurality of recombinant cell byproducts is a cell culturing medium.

Embodiment 113. The method of Embodiment 111 or Embodiment 112, wherein the composition comprising the recombinant protein and the plurality of recombinant cell byproducts is a cell culture medium comprising recombinant cells that secreted the recombinant protein and the plurality of recombinant cell byproducts.

Embodiment 114. The method of any one of Embodiments 111 to 113, wherein the composition comprising the recombinant protein and the plurality of recombinant cell byproducts has a pH greater than the isoelectric point (pI) of the recombinant protein.

Embodiment 115. The method of Embodiment 114, wherein the pH of the composition comprising the recombinant protein and the plurality of recombinant cell byproducts is not modified to achieve a pH greater than the pI of the recombinant protein.

Embodiment 116. The method of any one of Embodiments 111 to 115, wherein the flocculant is added to a culturing medium comprising recombinant cells that are secreting the recombinant protein and the plurality of recombinant cell byproducts.

Embodiment 117. The method of any one of Embodiments 111 to 116, wherein once the flocculant attaches to one or more components of the plurality of recombinant cell byproducts, the flocculant is separated from the recombinant protein.

Embodiment 118. The method of Embodiment 117, wherein when the flocculant attaches to one or more components of the plurality of recombinant cell byproducts is isolated from the recombinant protein with a strainer, a filtering apparatus, and/or by centrifugation.

Embodiment 119. The method of Embodiment 118, further comprising supplementing the culturing medium again with a flocculant.

Embodiment 120. The method of any one of Embodiments 111 to 119, wherein the flocculant is provided to a biomass separation feed tank and to one or more components of the plurality of recombinant cell byproducts contemporaneously with removal of spent biomass including recombinant cells.

Embodiment 121. The method of any one of Embodiments 111 to 119, wherein the flocculant is provided after removal of spent biomass including recombinant cells.

Embodiment 122. The method of Embodiment 121, wherein the composition comprising the recombinant protein and the plurality of recombinant cell byproducts lacks recombinant cells that secreted the recombinant protein and the plurality of recombinant cell byproducts.

Embodiment 123. The method of any one of Embodiments 111 to 122, wherein the flocculant is an anionic flocculant or a neutral flocculant.

Embodiment 124. The method of any one of Embodiments 111 to 123, wherein the flocculant is Tramfloc 108, Tramfloc 109, Tramfloc 110, Tramfloc 111 or Tramfloc 120, Magnafloc 333, Magnafloc 355, or Gusmer Divergan, Dupont Polyox, Celite 545, Bentonite BE125, DIAION HPA25L, Chitosan 85% deacetylated, EZ DE, ultrapure diatomaceous earth, or Relisorb SP400.

Embodiment 125. The method of any one of Embodiments 111 to 124, wherein the flocculant is provided in a column.

Embodiment 126. The method of any one of Embodiments 111 to 125, wherein the processing the composition under conditions that separate the recombinant protein from the plurality of recombinant cell byproducts further comprises a chromatography system.

Embodiment 127. The method of Embodiment 126, wherein the chromatography system operates in batch mode with an axial flow column or a radial flow column or a centrifugal column or by use of a membrane chromatography column or the chromatography system operates in a continuous mode comprising multiple columns in parallel, with the feed to the columns being switchable such that various steps in a chromatography process (e.g., equilibration, load, elute, and clean), occur contemporaneously.

Embodiment 128. The method of Embodiment 127, wherein the continuous mode comprises a simulated moving bed (SMB) or an Ion Separator (e.g., ISEP®) system.

Embodiment 129. The method of any one of Embodiments 121 to 128, wherein the composition comprising the recombinant protein and the plurality of recombinant cell byproducts was previously treated to remove spent biomass including recombinant cells and/or was previously treated to remove small non-protein molecules.

Embodiment 130. The method of Embodiment 129, wherein the treatment to remove small non-protein molecules comprises a step that concentrates the composition comprising the recombinant protein and the plurality of recombinant cell byproducts.

Embodiment 131. The method of Embodiment 129 or Embodiment 130, wherein the treatment to remove small non-protein molecules comprises a diafiltration buffer.

Embodiment 132. The method of any one of Embodiments 111 to 131 further comprising a concentration step and/or diafiltration treatment of the separated recombinant protein to produce a protein-containing composition having a preferred pH and/or ionic condition.

Embodiment 133. The method of Embodiment 132, wherein the protein-containing composition having a preferred pH and/or ionic condition is further heat treated and/or dried.

Embodiment 134. The method of any one of Embodiments 111 to 131, wherein the composition comprising the recombinant protein and the plurality of recombinant cell byproducts and/or the protein product having a reduced quantity of the plurality of recombinant cell byproducts is further heat treated and/or dried.

Embodiment 135. The method of Embodiment 133 or Embodiment 134, wherein the heat treatment separates the recombinant protein and the off-flavor component, wherein the heat is applied at a temperature and duration such that the off-flavor component is volatized and a gaseous off-flavor component is removable.

Embodiment 136. The method of Embodiment 135, wherein a vacuum is applied contemporaneous with the application of heat and the vacuum facilitates removal of the gaseous off-flavor component.

Embodiment 137. The method of any one of Embodiments 111 to 136, wherein the off-flavor component is an acid, an alcohol, an aldehyde, an aromatic, an ester, or a ketone.

Embodiment 138. The method of any one of Embodiments 111 to 137, wherein the off-flavor component is (E)-2-nonenal; 1-dodecene; 1-hexanol, 2-ethyl-; 1-hexen-3-one; 1-octen one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

Embodiment 139. The method of any one of Embodiments 133 to 138, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

Embodiment 140. The method any one of Embodiments 133 to 139, wherein the method comprises agitation during the heat treatment.

Embodiment 141. The method any one of Embodiments 133 to 140, wherein the heat treatment and/or drying step produces a dry protein product having a reduced quantity of the plurality of recombinant cell byproducts.

Embodiment 142. The method of any one of Embodiments 111 to 141, wherein the composition comprising the recombinant protein and the plurality of recombinant cell byproducts and/or the protein product having a reduced quantity of the plurality of recombinant cell byproducts further undergoes an oxidation step 143. The method of Embodiment 142, wherein the oxidization step comprises the addition of hydrogen peroxide.

Embodiment 144. The method of any one of Embodiments 111 to 143, wherein the ratio of the recombinant cell byproducts to recombinant protein in the composition comprising a recombinant protein and the plurality of recombinant cell byproducts is about 1:3 to about 3:1.

Embodiment 145. The method of Embodiment 144, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

Embodiment 146. The method of Embodiment 145, wherein less than about 10% of the weight of the protein product comprises recombinant cell byproducts.

Embodiment 147. The method of any one of Embodiments 111 to 146, wherein less than about 5% of the weight of the protein product comprises recombinant cell byproducts.

Embodiment 148. The method of any one of Embodiments 111 to 147, wherein less than about 5%, less than about 1%, less than about 0.1%, or less than about 0.01% of the weight of the protein product comprises the off-flavor component.

Embodiment 149. The method of any one of Embodiments 111 to 148, wherein the off-flavor component in the protein product is virtually undetectable to a standard consumer.

Embodiment 150. The method of any one of Embodiments 111 to 149, wherein the EPS is generally inseparable from the recombinant protein when using size exclusion chromatography.

Embodiment 151. The method of any one of Embodiments 111 to 150, wherein the EPS is naturally a component of a recombinant cell's cell wall.

Embodiment 152. The method of one of Embodiments 111 to 151, wherein the EPS has an apparent size of about 13 kDa to about 27 kDa as characterized by a size exclusion chromatography column.

Embodiment 153. The method of any one of Embodiments 111 to 152, wherein the EPS comprises mannose.

Embodiment 154. The method of any one of Embodiments 111 to 153, wherein the EPS further comprises N-acetylglucosamine and/or glucose.

Embodiment 155. The method of any one of Embodiments 111 to 154, wherein the EPS comprises about 91 mol % mannose, about 5 mol % N-acetylglucosamine, and about 3 mol % glucose as analyzed by gas chromatography in tandem with mass spectrometry.

Embodiment 156. The method of any one of Embodiments 111 to 155, wherein the EPS comprises an α(1,6)-linked backbone with α(1,2)-linked branches and/or α(1,3)-linked branches.

Embodiment 157. The method of any one of Embodiments 111 to 156, wherein the EPS is a mannan.

Embodiment 158. The method of any one of Embodiments 111 to 157, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

Embodiment 159. The method of any one of Embodiments 111 to 158, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

Embodiment 160. The method of Embodiment 158 or Embodiment 159, wherein the fungus is a *Pichia* species.

Embodiment 161. The method of Embodiment 160, wherein the *Pichia* species is *Komagataella phaffii* or *Komagataella pastoris*.

Embodiment 162. The method of any one of Embodiments 111 to 161, wherein the recombinant protein is an enzyme, a nutritive protein, a food ingredient, or a food additive.

Embodiment 163. The method of Embodiment 162, wherein the enzyme is pepsinogen or pepsin.

Embodiment 164. The method of Embodiment 163, wherein the protein is an egg-white protein.

Embodiment 165. The method of Embodiment 164, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

Embodiment 166. The method of Embodiment 164 or Embodiment 165, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

Embodiment 167. The method of any one of Embodiments 111 to 166, wherein the consumable composition comprising the protein product comprises food products, beverage products, or dietary supplements.

Embodiment 168. The method of Embodiment 167, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

Embodiment 169. The method of Embodiment 167, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

Embodiment 170. The method of Embodiment 167, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

Embodiment 171. The method of any one of Embodiments 111 to 170, wherein the processing the composition under conditions that separate the recombinant protein from the plurality of recombinant cell byproducts further comprises one or more of: i) a cationic resin that reversibly attaches to the recombinant protein and does not substantially attach to the EPS, ii) an anionic resin that reversibly attaches to the recombinant protein and does not substantially attach to the EPS, iii) an enzyme that digests the recombinant protein or the EPS, and/or iv) an adsorbent that attaches to the EPS and does not substantially attach to the recombinant protein.

Embodiment 172. A consumable composition obtained by the method of any one of Embodiments 111 to 171.

Embodiment 173. A method for preparing a consumable composition, the method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an adsorbent that reversibly attaches to one or more components of the plurality of recombinant cell byproducts and does not substantially attach to the recombinant protein; collecting the separated recombinant protein, thereby obtaining a protein product having a reduced quantity of the plurality of recombinant cell byproducts; and formulating a consumable composition comprising the protein product.

Embodiment 174. The method of Embodiment 173, wherein the composition comprising the recombinant protein and the plurality of recombinant cell byproducts is a cell culturing medium.

Embodiment 175. The method of Embodiment 173 or Embodiment 174, wherein the composition comprising the recombinant protein and the plurality of recombinant cell byproducts is a cell culture medium comprising recombinant cells that secreted the recombinant protein and the plurality of recombinant cell byproducts.

Embodiment 176. The method of any one of Embodiments 173 to 175, wherein the composition comprising the recombinant protein and the plurality of recombinant cell byproducts has a pH greater than the isoelectric point (pI) of the recombinant protein.

Embodiment 177. The method of Embodiment 176, wherein the pH of the composition comprising the recombinant protein and the plurality of recombinant cell byproducts is not modified to achieve a pH greater than the pI of the recombinant protein.

Embodiment 178. The method of any one of Embodiments 173 to 177, wherein the adsorbent is added to a culturing medium comprising recombinant cells that are secreting the recombinant protein and the plurality of recombinant cell byproducts.

Embodiment 179. The method of any one of Embodiments 173 to 178, wherein once the adsorbent attaches to one or more components of the plurality of recombinant cell byproducts, the adsorbent is separated from the recombinant protein.

Embodiment 180. The method of Embodiment 179, wherein when the adsorbent attaches to one or more components of the plurality of recombinant cell byproducts is isolated from the recombinant protein with a strainer, a filtering apparatus, and/or by centrifugation.

Embodiment 181. The method of Embodiment 180, further comprising supplementing the culturing medium again with a adsorbent.

Embodiment 182. The method of any one of Embodiments 173 to 181, wherein the adsorbent is provided to a biomass separation feed tank and to one or more components of the plurality of recombinant cell byproducts contemporaneously with removal of spent biomass including recombinant cells.

Embodiment 183. The method of any one of Embodiments 173 to 181, wherein the adsorbent is provided after removal of spent biomass including recombinant cells.

Embodiment 184. The method of Embodiment 183, wherein the composition comprising the recombinant protein and the plurality of recombinant cell byproducts lacks recombinant cells that secreted the recombinant protein and the plurality of recombinant cell byproducts.

Embodiment 185. The method of any one of Embodiments 173 to 184, wherein adsorbent comprises a resin and/or a hydrophobic adsorbent e.g., comprising a methacrylate or a silica backbone or is a DEAE type weak anion exchanger.

Embodiment 186. The method of any one of Embodiments 173 to 185, wherein the adsorbent is Dow Amberlite SD2, Mitsubishi Diaion HP20, Celite 545, Bentonite BE125, DIAION HPA25L, Chitosan 85% deacetylated, EZ DE, ultrapure diatomaceous earth, or Relisorb SP400.

Embodiment 187. The method of any one of Embodiments 173 to 186, wherein the adsorbent is provided in a column, e.g., and operated in batch mode with an axial flow column or a radial flow column or a centrifugal column or by use of a membrane chromatography column.

Embodiment 188. The method of any one of Embodiments 173 to 187, wherein the processing the composition under conditions that separate the recombinant protein from the plurality of recombinant cell byproducts further comprises a chromatography system.

Embodiment 189. The method of Embodiment 188, wherein the chromatography system operates in batch mode with an axial flow column or a radial flow column or a centrifugal column or by use of a membrane chromatography column or the chromatography system operates in a continuous mode comprising multiple columns in parallel, with the feed to the columns being switchable such that various steps in a chromatography process (e.g., equilibration, load, elute, and clean), occur contemporaneously.

Embodiment 190. The method of Embodiment 189, wherein the continuous mode comprises a simulated moving bed (SMB) or an Ion Separator (e.g., ISEP®) system.

Embodiment 191. The method of any one of Embodiments 183 to 190, wherein the composition comprising the recombinant protein and the plurality of recombinant cell byproducts was previously treated to remove spent biomass including recombinant cells and/or was previously treated to remove small non-protein molecules.

Embodiment 192. The method of Embodiment 191, wherein the treatment to remove small non-protein molecules comprises a step that concentrates the composition comprising the recombinant protein and the plurality of recombinant cell byproducts.

Embodiment 193. The method of Embodiment 191 or Embodiment 192, wherein the treatment to remove small non-protein molecules comprises a diafiltration buffer.

Embodiment 194. The method of any one of Embodiments 173 to 193 further comprising a concentration step and/or diafiltration treatment of the separated recombinant protein to produce a protein-containing composition having a preferred pH and/or ionic condition.

Embodiment 195. The method of Embodiment 194, wherein the protein-containing composition having a preferred pH and/or ionic condition is further heat treated and/or dried.

Embodiment 196. The method of any one of Embodiments 173 to 193, wherein the composition comprising the recombinant protein and the plurality of recombinant cell byproducts and/or the protein product having a reduced quantity of the plurality of recombinant cell byproducts is further heat treated and/or dried.

Embodiment 197. The method of Embodiment 195 or Embodiment 196, wherein the heat treatment separates the recombinant protein and the off-flavor component, wherein the heat is applied at a temperature and duration such that the off-flavor component is volatized and a gaseous off-flavor component is removable.

Embodiment 198. The method of Embodiment 197, wherein a vacuum is applied contemporaneous with the application of heat and the vacuum facilitates removal of the gaseous off-flavor component.

Embodiment 199. The method of any one of Embodiments 173 to 198, wherein the off-flavor component is an acid, an alcohol, an aldehyde, an aromatic, an ester, or a ketone.

Embodiment 200. The method of any one of Embodiments 173 to 199, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

Embodiment 201. The method of any one of Embodiments 195 to 200, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

Embodiment 202. The method any one of Embodiments 195 to 201, wherein the method comprises agitation during the heat treatment.

Embodiment 203. The method any one of Embodiments 195 to 202, wherein the heat treatment and/or drying step produces a dry protein product having a reduced quantity of the plurality of recombinant cell byproducts.

Embodiment 204. The method of any one of Embodiments 173 to 203, wherein the composition comprising the recombinant protein and the plurality of recombinant cell byproducts and/or the protein product having a reduced quantity of the plurality of recombinant cell byproducts further undergoes an oxidation step.

Embodiment 205. The method of Embodiment 204, wherein the oxidization step comprises the addition of hydrogen peroxide.

Embodiment 206. The method of any one of Embodiments 173 to 205, wherein the ratio of the recombinant cell byproducts to recombinant protein in the composition comprising a recombinant protein and the plurality of recombinant cell byproducts is about 1:3 to about 3:1.

Embodiment 207. The method of Embodiment 206, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

Embodiment 208. The method of Embodiment 207, wherein less than about 10% of the weight of the protein product comprises recombinant cell byproducts.

Embodiment 209. The method of any one of Embodiments 173 to 208, wherein less than about 5% of the weight of the protein product comprises recombinant cell byproducts.

Embodiment 210. The method of any one of Embodiments 173 to 209, wherein less than about 5%, less than about 1%, less than about 0.1%, or less than about 0.01% of the weight of the protein product comprises the off-flavor component.

Embodiment 211. The method of any one of Embodiments 173 to 210, wherein the off-flavor component in the protein product is virtually undetectable to a standard consumer.

Embodiment 212. The method of any one of Embodiments 173 to 211, wherein the EPS is generally inseparable from the recombinant protein when using size exclusion chromatography.

Embodiment 213. The method of any one of Embodiments 173 to 212, wherein the EPS is naturally a component of a recombinant cell's cell wall.

Embodiment 214. The method of one of Embodiments 173 to 213, wherein the EPS has an apparent size of about 13 kDa to about 27 kDa as characterized by a size exclusion chromatography column.

Embodiment 215. The method of any one of Embodiments 173 to 214, wherein the EPS comprises mannose.

Embodiment 216. The method of any one of Embodiments 173 to 215, wherein the EPS further comprises N-acetylglucosamine and/or glucose.

Embodiment 217. The method of any one of Embodiments 173 to 216, wherein the EPS comprises about 91 mol % mannose, about 5 mol % N-acetylglucosamine, and about 3 mol % glucose as analyzed by gas chromatography in tandem with mass spectrometry.

Embodiment 218. The method of any one of Embodiments 173 to 217, wherein the EPS comprises an α(1,6)-linked backbone with α(1,2)-linked branches and/or α(1,3)-linked branches.

Embodiment 219. The method of any one of Embodiments 173 to 218, wherein the EPS is a mannan.

Embodiment 220. The method of any one of Embodiments 173 to 219, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

Embodiment 221. The method of any one of Embodiments 173 to 220, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

Embodiment 222. The method of Embodiment 220 or Embodiment 221, wherein the fungus is a *Pichia* species.

Embodiment 223. The method of Embodiment 222, wherein the *Pichia* species is *Komagataella phaffii* or *Komagataella pastoris*.

Embodiment 224. The method of any one of Embodiments 173 to 223, wherein the recombinant protein is an enzyme, a nutritive protein, a food ingredient, or a food additive.

Embodiment 225. The method of Embodiment 224, wherein the enzyme is pepsinogen or pepsin.

Embodiment 226. The method of Embodiment 225, wherein the protein is an egg-white protein.

Embodiment 227. The method of Embodiment 226, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

Embodiment 228. The method of Embodiment 226 or Embodiment 227, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

Embodiment 229. The method of any one of Embodiments 173 to 228, wherein the consumable composition comprising the protein product comprises food products, beverage products, or dietary supplements.

Embodiment 230. The method of Embodiment 229, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

Embodiment 231. The method of Embodiment 229, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

Embodiment 232. The method of Embodiment 229, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

Embodiment 233. The method of any one of Embodiments 173 to 232, wherein the processing the composition under conditions that separate the recombinant protein from the plurality of recombinant cell byproducts further comprises one or more of: one or more of: i) a cationic resin that reversibly attaches to the recombinant protein and does not substantially attach to the EPS, ii) an anionic resin that reversibly attaches to the recombinant protein and does not substantially attach to the EPS, iii) an enzyme that digests the recombinant protein or the EPS, and/or iv) a flocculant that attaches to the EPS and does not substantially attach to the recombinant protein.

Embodiment 234. A consumable composition obtained by the method of any one of Embodiments 173 to 233.

Embodiment 235. A method for preparing a consumable composition, the method comprising steps of: obtaining a composition comprising a recombinant protein and a plurality of recombinant cell byproducts, wherein the recombinant cell byproducts comprise an exopolysaccharide (EPS) and an off-flavor component; processing the composition under conditions that separate the recombinant protein from the plurality of recombinant cell byproducts, wherein the processing step comprises an enzyme that either digests the recombinant protein or digests the EPS; collecting the separated recombinant protein, thereby obtaining a protein product having a reduced quantity of the plurality of recombinant cell byproducts; and formulating a consumable composition comprising the protein product.

Embodiment 236. The method of Embodiment 235, wherein the composition comprising the recombinant protein and the plurality of recombinant cell byproducts is a cell culturing medium.

Embodiment 237. The method of Embodiment 235 or Embodiment 236, wherein the composition comprising the recombinant protein and the plurality of recombinant cell byproducts is a cell culture medium comprising recombinant cells that secreted the recombinant protein and the plurality of recombinant cell byproducts.

Embodiment 238. The method of Embodiment 235, wherein the composition comprising the recombinant protein and the plurality of recombinant cell byproducts lacks recombinant cells that secreted the recombinant protein and the plurality of recombinant cell byproducts.

Embodiment 239. The method of any one of Embodiments 235 to 238, wherein the composition comprising the recombinant protein and the plurality of recombinant cell byproducts has a pH greater than the isoelectric point (pI) of the recombinant protein.

Embodiment 240. The method of Embodiment 239, wherein the pH of the composition comprising the recombinant protein and the plurality of recombinant cell byproducts is not modified to achieve a pH greater than the pI of the recombinant protein.

Embodiment 241. The method of Embodiment 239, wherein the pH of the composition comprising the recombinant protein and the plurality of recombinant cell byproducts is modified to achieve a pH greater than the pI of the recombinant protein.

Embodiment 242. The method of Embodiment 240, wherein the pH of the composition comprising the recombinant protein and the plurality of recombinant cell byproducts is about 6.

Embodiment 243. The method of any one of Embodiments 235 to 238, wherein the composition comprising the recombinant protein and the plurality of recombinant cell byproducts has a pH less than the isoelectric point (pI) of the recombinant protein.

Embodiment 244. The method of Embodiment 243, wherein the pH of the composition comprising the recombinant protein and the plurality of recombinant cell byproducts achieved by lowering the pH.

Embodiment 245. The method of any one of Embodiments 235 to 244, wherein the enzyme that digests the recombinant protein is pepsin or trypsin.

Embodiment 246. The method of Embodiment 245, wherein the digested recombinant protein permeates through an ultrafiltration system with a 10 kDa membrane.

Embodiment 247. The method of any one of Embodiments 235 to 244, wherein the enzyme that digests the EPS is a mannase, a cellulase, or glucanase.

Embodiment 248. The method of Embodiment 247, wherein undigested recombinant protein is concentrated by ultrafiltration system with a 5 kDa membrane.

Embodiment 249. The method of any one of Embodiments 235 to 248, wherein the processing the composition under conditions that separate the recombinant protein from the plurality of recombinant cell byproducts further comprises a chromatography system.

Embodiment 250. The method of Embodiment 249, wherein the chromatography system operates in batch mode with an axial flow column or a radial flow column or a centrifugal column or by use of a membrane chromatography column.

Embodiment 251. The method of Embodiment 249, wherein the chromatography system operates in a continuous mode comprising multiple columns in parallel, with the feed to the columns being switchable such that various steps in a chromatography process (e.g., equilibration, load, elute, and clean), occur contemporaneously.

Embodiment 252. The method of Embodiment 251, wherein the continuous mode comprises a simulated moving bed (SMB) or an Ion Separator (e.g., ISEP®) system.

Embodiment 253. The method of any one of Embodiments 245 to 252, wherein the composition comprising the recombinant protein and the plurality of recombinant cell byproducts was previously treated to remove spent biomass including recombinant cells and/or was previously treated to remove small non-protein molecules.

Embodiment 254. The method of Embodiment 253, wherein the treatment to remove small non-protein molecules comprises a step that concentrates the composition comprising the recombinant protein and the plurality of recombinant cell byproducts.

Embodiment 255. The method of Embodiment 253 or Embodiment 254, wherein the treatment to remove small non-protein molecules comprises a diafiltration buffer.

Embodiment 256. The method of any one of Embodiments 235 to 255 further comprising a concentration step and/or diafiltration treatment of the separated recombinant protein to produce a protein-containing composition having a preferred pH and/or ionic condition.

Embodiment 257. The method of Embodiment 256, wherein the protein-containing composition having a preferred pH and/or ionic condition is further heat treated and/or dried.

Embodiment 258. The method of any one of Embodiments 235 to 255, wherein the composition comprising the recombinant protein and the plurality of recombinant cell byproducts and/or the protein product having a reduced quantity of the plurality of recombinant cell byproducts is further heat treated and/or dried.

Embodiment 259. The method of Embodiment 257 or Embodiment 258, wherein the heat treatment separates the recombinant protein and the off-flavor component, wherein the heat is applied at a temperature and duration such that the off-flavor component is volatized and a gaseous off-flavor component is removable.

Embodiment 260. The method of Embodiment 259, wherein a vacuum is applied contemporaneous with the application of heat and the vacuum facilitates removal of the gaseous off-flavor component.

Embodiment 261. The method of any one of Embodiments 235 to 260, wherein the off-flavor component is an acid, an alcohol, an aldehyde, an aromatic, an ester, or a ketone.

Embodiment 262. The method of any one of Embodiments 235 to 261, wherein the off-flavor component is (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; or propanoic acid, 2-methyl-, 3-hydroxy-2,4,4-trimethylpentyl ester.

Embodiment 263. The method of any one of Embodiments 257 to 262, wherein the temperature of the protein-containing composition having a preferred pH and/or ionic conditions, the composition comprising the recombinant protein and the plurality of recombinant cell byproducts, and/or the protein product having a reduced quantity of the plurality of recombinant cell byproducts during the heat treatment is up to 80° C., e.g., from about 50° C. to about 60° C.

Embodiment 264. The method any one of Embodiments 257 to 263, wherein the method comprises agitation during the heat treatment.

Embodiment 265. The method any one of Embodiments 257 to 264, wherein the heat treatment and/or drying step produces a dry protein product having a reduced quantity of the plurality of recombinant cell byproducts.

Embodiment 266. The method of any one of Embodiments 235 to 265, wherein the composition comprising the recombinant protein and the plurality of recombinant cell byproducts and/or the protein product having a reduced quantity of the plurality of recombinant cell byproducts further undergoes an oxidation step.

Embodiment 267. The method of Embodiment 266, wherein the oxidization step comprises the addition of hydrogen peroxide.

Embodiment 268. The method of any one of Embodiments 235 to 267, wherein the ratio of the recombinant cell byproducts to recombinant protein in the composition comprising a recombinant protein and the plurality of recombinant cell byproducts is about 1:3 to about 3:1.

Embodiment 269. The method of Embodiment 268, wherein the protein product has an at least 25% reduction, an at least 30% reduction, an at least 35% reduction, an at least 40% reduction, an at least 45% reduction, an at least 50% reduction, an at least 55% reduction, an at least 60% reduction, an at least 65% reduction, an at least 70% reduction, an at least 75% reduction an at least 75% reduction, at least 80% reduction, at least 90% reduction, or at least 95% reduction in the quantity of EPS and/or the quantity of off-flavor components relative to the composition comprising a recombinant protein and the plurality of recombinant cell byproducts.

Embodiment 270. The method of Embodiment 269, wherein less than about 10% of the weight of the protein product comprises recombinant cell byproducts.

Embodiment 271. The method of any one of Embodiments 235 to 270, wherein less than about 5% of the weight of the protein product comprises recombinant cell byproducts.

Embodiment 272. The method of any one of Embodiments 235 to 271, wherein less than about 5%, less than about 1%, less than about 0.1%, or less than about 0.01% of the weight of the protein product comprises the off-flavor component.

Embodiment 273. The method of any one of Embodiments 235 to 272, wherein the off-flavor component in the protein product is virtually undetectable to a standard consumer.

Embodiment 274. The method of any one of Embodiments 235 to 273, wherein the EPS is generally inseparable from the recombinant protein when using size exclusion chromatography.

Embodiment 275. The method of any one of Embodiments 235 to 274, wherein the EPS is naturally a component of a recombinant cell's cell wall.

Embodiment 276. The method of one of Embodiments 235 to 275, wherein the EPS has an apparent size of about 13 kDa to about 27 kDa as characterized by a size exclusion chromatography column.

Embodiment 277. The method of any one of Embodiments 235 to 276, wherein the EPS comprises mannose.

Embodiment 278. The method of any one of Embodiments 235 to 277, wherein the EPS further comprises N-acetylglucosamine and/or glucose.

Embodiment 279. The method of any one of Embodiments 235 to 278, wherein the EPS comprises about 91 mol % mannose, about 5 mol % N-acetylglucosamine, and about 3 mol % glucose as analyzed by gas chromatography in tandem with mass spectrometry.

Embodiment 280. The method of any one of Embodiments 235 to 279, wherein the EPS comprises an $\alpha(1,6)$-linked backbone with $\alpha(1,2)$-linked branches and/or $\alpha(1,3)$-linked branches.

Embodiment 281. The method of any one of Embodiments 235 to 280, wherein the EPS is a mannan.

Embodiment 282. The method of any one of Embodiments 235 to 281, wherein the recombinant cell that expresses the recombinant protein and the plurality of recombinant cell byproducts is selected from a fungal cell, such as filamentous fungus or a yeast, a bacterial cell, a plant cell, an insect cell, or a mammalian cell.

Embodiment 283. The method of any one of Embodiments 235 to 282, wherein the recombinant cell type is selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculo sum*, *Penicillium purpurogenum*, *Penicillium roqueforti*, *Pleurotus* spp., *Pleurotus ostreatus*, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma vireus*.

Embodiment 284. The method of Embodiment 282 or Embodiment 283, wherein the fungus is a *Pichia* species.

Embodiment 285. The method of Embodiment 284, wherein the *Pichia* species is *Komagataella phaffii* or *Komagataella pastoris*.

Embodiment 286. The method of any one of Embodiments 235 to 285, wherein the recombinant protein is an enzyme, a nutritive protein, a food ingredient, or a food additive.

Embodiment 287. The method of Embodiment 286, wherein the enzyme is pepsinogen or pepsin.

Embodiment 288. The method of Embodiment 287, wherein the protein is an egg-white protein.

Embodiment 289. The method of Embodiment 288, wherein the egg-white protein is ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, or ovalbumin related protein Y, and any combination thereof.

Embodiment 290. The method of Embodiment 288 or Embodiment 289, wherein the egg-white protein has a sequence that at least 80% identical (e.g., about 85%, 90%, or 95% identical) to the egg-white protein naturally produced in a bird, e.g., a chicken, quail, turkey, turkey vulture, hummingbird, duck, ostrich, goose, gull, guineafowl, pheasant, or emu.

Embodiment 291. The method of any one of Embodiments 235 to 290, wherein the consumable composition comprising the protein product comprises food products, beverage products, or dietary supplements.

Embodiment 292. The method of Embodiment 291, wherein the food products comprise baked goods (e.g., cake, muffin, cookie, bread, bagel, pastry, doughnut), scramble, omelet, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings.

Embodiment 293. The method of Embodiment 291, wherein the beverage products comprise soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks.

Embodiment 294. The method of Embodiment 291, wherein the dietary supplements comprise multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement.

Embodiment 295. The method of any one of Embodiments 235 to 294, wherein the processing the composition under conditions that separate the recombinant protein from the plurality of recombinant cell byproducts further comprises one or more of: i) a cationic resin that reversibly attaches to the recombinant protein and does not substantially attach to the EPS, ii) an anionic resin that reversibly attaches to the recombinant protein and does not substantially attach to the EPS, iii) a flocculant that attaches to the EPS and does not substantially attach to the recombinant protein, and/or iv) an adsorbent that attaches to the EPS and does not substantially attach to the recombinant protein.

Embodiment 296. A consumable composition obtained by the method of any one of Embodiments 235 to 295.

Additionally, of the above embodiments described herein can be combined with any other embodiment as disclosed above.

EXAMPLES

Example 1: Use of a Resin for Preparing a Protein Product Having a Reduced Quantity of a Recombinant Cell Byproduct A method of the present disclosure (e.g., as shown in FIG. 1) was used to prepare a protein product having a reduced quantity of a recombinant cell byproduct. In this example, a recombinant egg-white protein was used.

Table 1 (below) shows a typical composition comprising a recombinant protein and a recombinant cell byproduct before and after the use of resin-based (e.g., chromatography) purification process to reduce the quantity of the recombinant cell byproduct.

TABLE 1

Comparison of physio chemical properties of the concentrated protein before and after the purification step.

| | Concentrated protein | Purified protein |
|---|---|---|
| Protein (% w/w) | 53 | 98 |
| EPS (% w/w) | 47 | 2 |

The purified protein was further used to demonstrate unique gelling properties similar to commercial egg whites thereby enabling formulation replacing eggs in the egg-based recipes.

Table 2, below, shows a comparison of the concentrated composition (comprising the recombinant protein and a recombinant cell byproduct) and purified protein product (which has reduced quantity of the recombinant cell byproduct) further for various functional properties is shown in the following table.

TABLE 2

Comparison of functional properties of the concentrated protein before and after the purification step.

| | Concentrated protein | Purified protein |
|---|---|---|
| Gel hardness | High | low |
| Chewiness | High | Low |
| Foam capacity | High | High |
| Foam stability | Low | high |

Notably, removing the recombinant cell byproduct (e.g., EPS) reduced the gel hardness and chewiness of an illustrative consumable composition/food product relative.

Table 3, below, shows a comparison of the functional properties of the concentrated composition (comprising the recombinant protein and a recombinant cell byproduct) and a commercial-available egg substitute further for various functional properties.

TABLE 3

Comparison of functional properties of the concentrated composition (comprising the recombinant protein and a recombinant cell byproduct) to a commercial egg white protein

| | Concentrated protein | Egg white protein |
|---|---|---|
| Gel hardness | High | High |
| Chewiness | High | High |
| Foam capacity | High | High |

Surprisingly, it was discovered that the gelation characteristics of the concentrated composition (comprising the recombinant protein and a recombinant cell byproduct) was equivalent to an egg white powder, indicating significant contribution of the impurities towards gelation. Further, the foaming and foam retention properties as shown in Table 2. Thus, for high foam applications, it may be preferable to specifically modulate the quantities of the recombinant cell byproducts in a consumable composition.

A purified recombinant ovalbumin protein product was combined with various amounts of the recombinant cell byproduct (e.g., EPS or off-flavor component) to determine changes in product properties.

Resins with sulfopropyl, sulfomethyl, sulfonate may be used in this method. The backbone is typically a nonprotein binding material such as methacrylate or cellulose with typical particle size between 50-200 um. The ligand density would accommodate protein binding capacity between 50-100 g protein/L resin.

Figure 7:
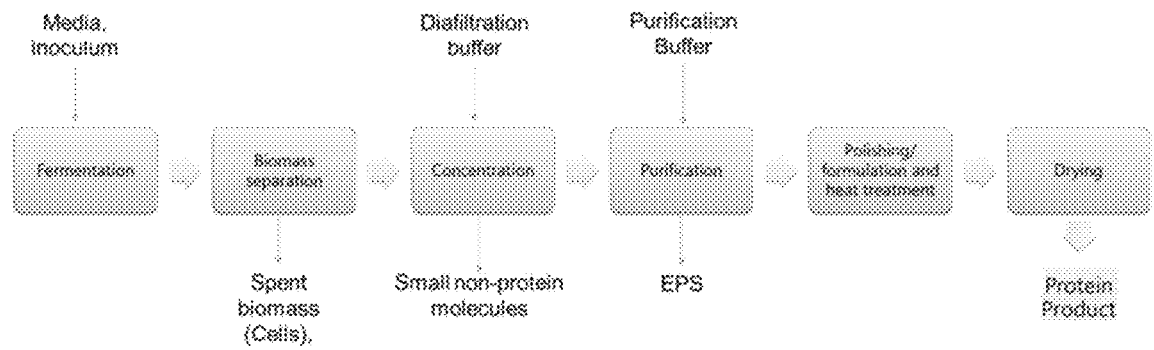
Figure 8:
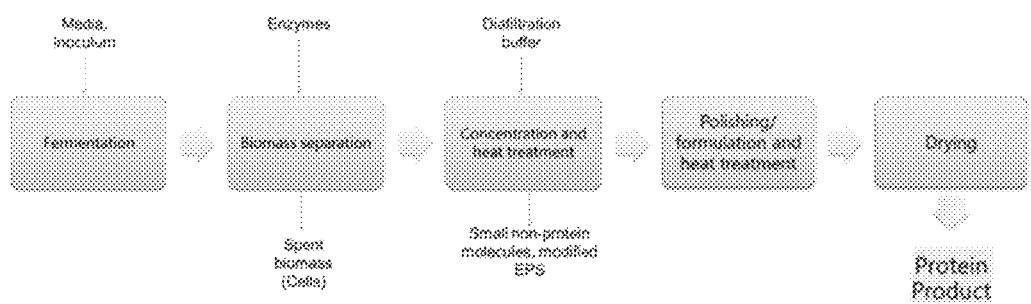
Figure 9:
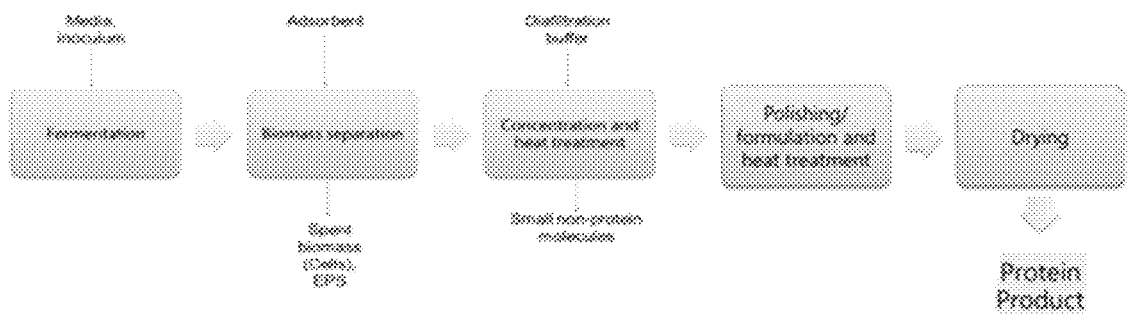
Figure 10:
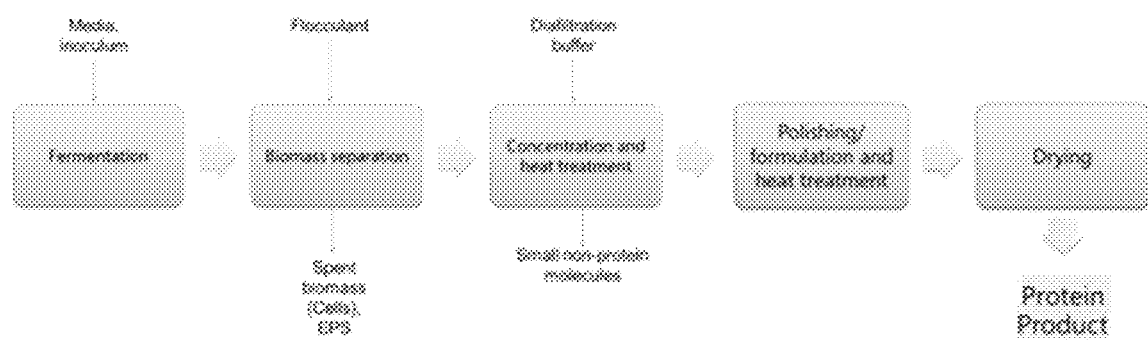

Example 2: Another Use of a Resin for Preparing a Protein Product Having a Reduced Quantity of a Recombinant Cell Byproduct Another method of the present disclosure (e.g., as shown in FIG. 1 or FIG. 7) was used to prepare a protein product having a reduced quantity of a recombinant cell byproduct. In this example, a recombinant egg-white protein was used.

Pichia Pastoris strain derived from the historic Phillips Petroleum strain NRRL Y-11430 was designed to generate a nonmethanol-utilization (mutM) phenotype with transformations to express an illustrative protein, here ovomucoid, and a strong methanol inducible promoter. These transformant strains were further modified by adding a surface display enzyme that would reduce the complex carbohydrate to filterable size. Sequencing confirmed that this strain did not contain any antibiotic markers or prokaryotic vector origin of replication sequences.

The resulting strain was grown in fermentation conditions in high-density growth conditions at about pH 5. After about 36 hours of growth under fermentation conditions, the pH was raised to about pH 6, and expression of the illustrative protein was induced by the addition of methanol to the culture. The fermentation broth was centrifuged (using a bench centrifuge-Avant J18 rotor Bechman Coulter) to remove cells. This was followed by filtration of the supernatant using a 0.2 μm hollow fiber membrane filtration to remove host protein and cell debris. The protein solution was then concentrated using a 5 kDa ultrafiltration membrane to over 30 g/L protein and diafiltered extensively to remove most of the organic and inorganic impurities. The resulting protein concentrate was adjusted to pH 3.5 using citrate and loaded on to a chromatography column. This column was packed with Cation exchange resin (SP400, Mitsubishi Chemicals, Japan). The chromatography steps were carried out with an AKTA Explorer 900 (GE Healthcare Life Sciences) and the Unicorn interface software (version 5.11) at approximately 22° C. in a down-flow mode. the chromatography method generally consisted of an equilibration step, a load (flowthrough) step, a wash step to remove non-bound protein, an elution step to remove product, a cleaning in place (CIP) step and regeneration step. The column volumes of elution, at each step and the buffer used is shown in the following Table 4.

TABLE 4

List of buffers and the column volumes required in a typical process.

| Step | Number of Column Volumes | Buffer composition |
|---|---|---|
| Equilibration | 4 | 25 mM Citrate buffer |
| Sample application | 1-2 | Feed sample |
| Column Wash | 2-3 | 25 mM Citrate buffer |
| Elution | 3-4 | 25 mM Citrate buffer with 1M NaCl |

TABLE 4-continued

List of buffers and the column volumes required in a typical process.

| Step | Number of Column Volumes | Buffer composition |
|---|---|---|
| CIP | 3 | 1M NaOH |
| Regeneration | 3 | 20% EtOH and 150 mM NaCl |

Figure 12:
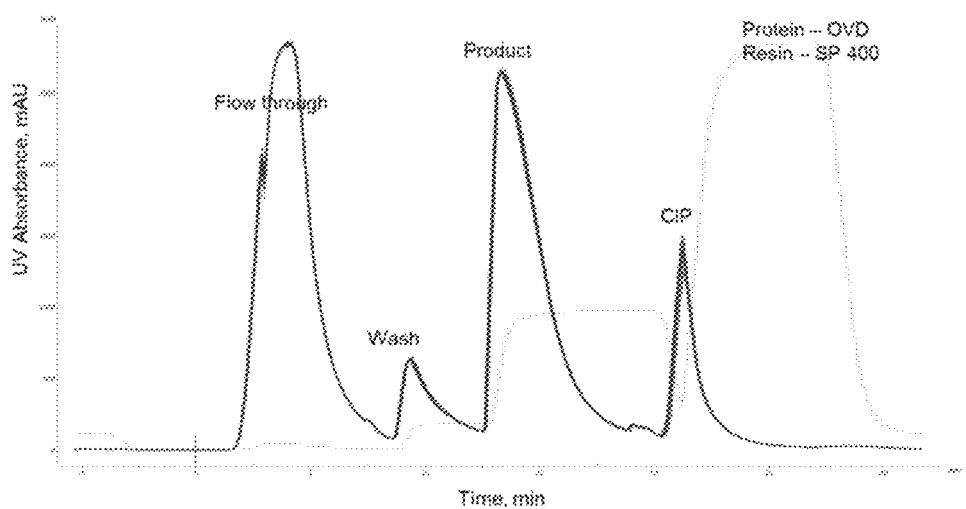
FIG. 12 is a chromatogram of a process using SP 400 resin for purification of an illustrative protein. n=3, dotted line showing conductivity.

The elution profile is shown in FIG. 12.

In this and other examples, the following terms are used: "Equilibration" is preloading a column, "Flow through" is the material passing the column when the UF diafiltered concentrate is passed through it and shown as lane 3 on the gel and minimal product loss, "Elute" is the protein of interest rich fraction (e.g., in the gel of FIG. 14, in lane 4) and the biggest peak in the chromatogram, "CIP" is the cleaning solution elution.

Figure 13:
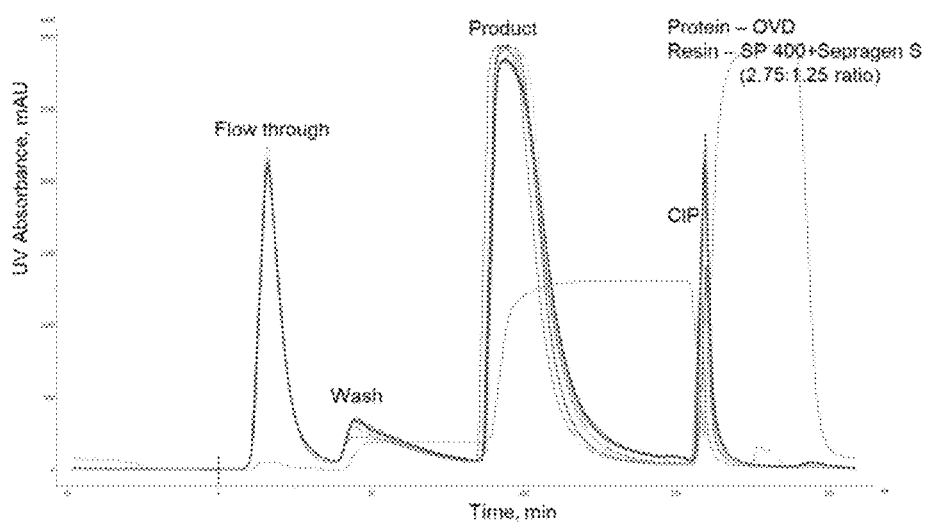
FIG. 13 is a chromatogram of a process using a combination of SP 400 and Sepragen S resin (2.75:1.25 ratio) for purification of an illustrative protein. n=3, dotted line showing conductivity.

In an alternate method, the column is packed with a unique mixture of two resins. SP400 (Mitsubishi Chemicals, Japan) and Sepragen S (Sepragen, Calif.) in the ratio of 2.75:1.25. The buffer compositions and the column volumes are maintained as shown in Table 4. The elution profile is shown in FIG. 13.

Resins with sulfopropyl, sulfomethyl, sulfonate may be used in this method. The backbone is typically a nonprotein binding material such as methacrylate or cellulose with typical particle size between 50-200 um. The ligand density would accommodate protein binding capacity between 50-100 g protein/L resin.

Example 3: An Anionic Resin for Preparing a Protein Product Having a Reduced Quantity of a Recombinant Cell Byproduct In Example 2, the column was packed with a cationic resin. In the present example, the column is packed with anionic exchange capto Q resin (Cytiva Chemicals). The buffer compositions and the column volumes are maintained as shown in Table 5. Note that the feed is not pH modified here simplifying the process significantly. Note that the feed is not pH modified here simplifying the process significantly.

TABLE 5

List of buffers and the column volumes required in a typical process.

| Step | Number of Column Volumes | Buffer composition |
|---|---|---|
| Equilibration | 4 | 25 mM Sodium Phosphate + 16 mM Sodium Chloride (pH 6; Conductivity—3.4 mS/cm) |
| Sample application | 1-2 | Feed sample diluted to 3.4 mS/cm |
| Column Wash | 2-3 | Same as equilibration |
| Elution | 3-4 | 25 mM Sodium Phosphate + 300 mM Sodium Chloride |
| CIP | 3 | 1M NaOH |
| Regeneration | 3 | 20% EtOH and 16 mM NaCl |

Figure 14A:
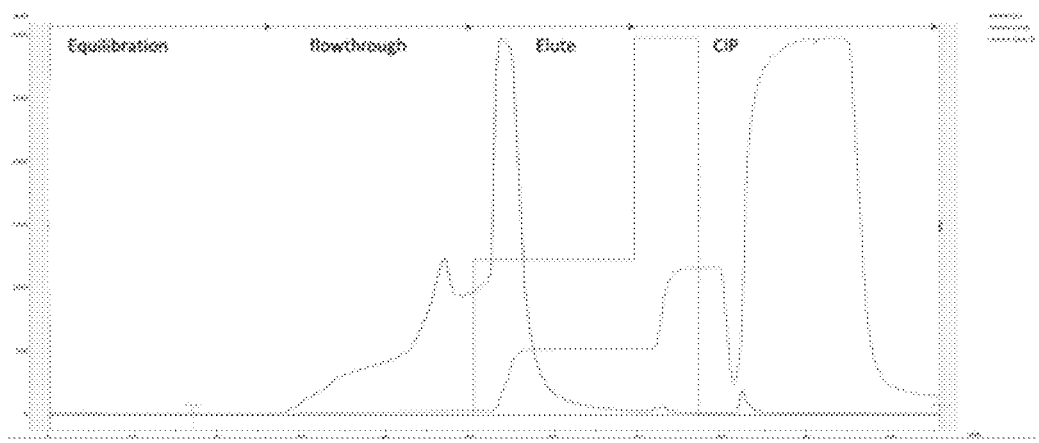
FIG. 14A is a chromatogram of the fractions in a process using anion exchange Capto Q resin for purification of an illustrative protein. The curved line with the first two rounded peaks showing protein elution (280 nm), the angular line shows the elution buffer B used in the process and the curve shows the usage during the process, the curve with the final peak shows conductivity (as, expected conductivity is high during protein elution and very high during CIP elution).
Figure 14B:
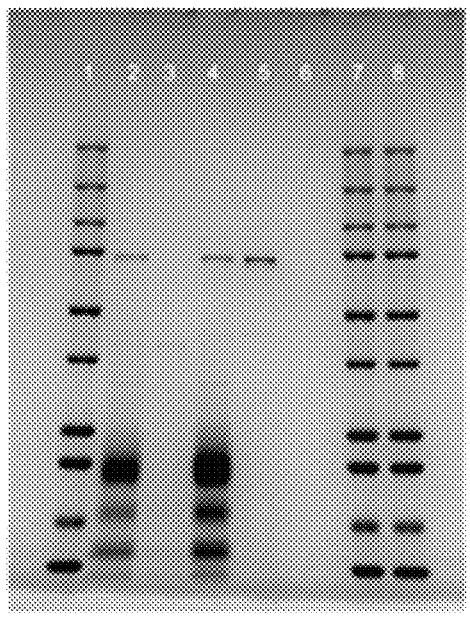
FIG. 14B is an SDS-PAGE gel of the fractions shown in FIG. 14A. Lane 2 is the feed, lane 3 is the flow through, lane 4 is the elute, and lane 5 is the cleaning in place (CIP).

The elution profile is shown in FIG. 14A and a gel showing the protein fractions is shown in FIG. 14B.

Resins with trimethyl aminoethyl, triethyl aminoethyl, quaternary amine groups may be used in methods described in this example.

Figure 15:
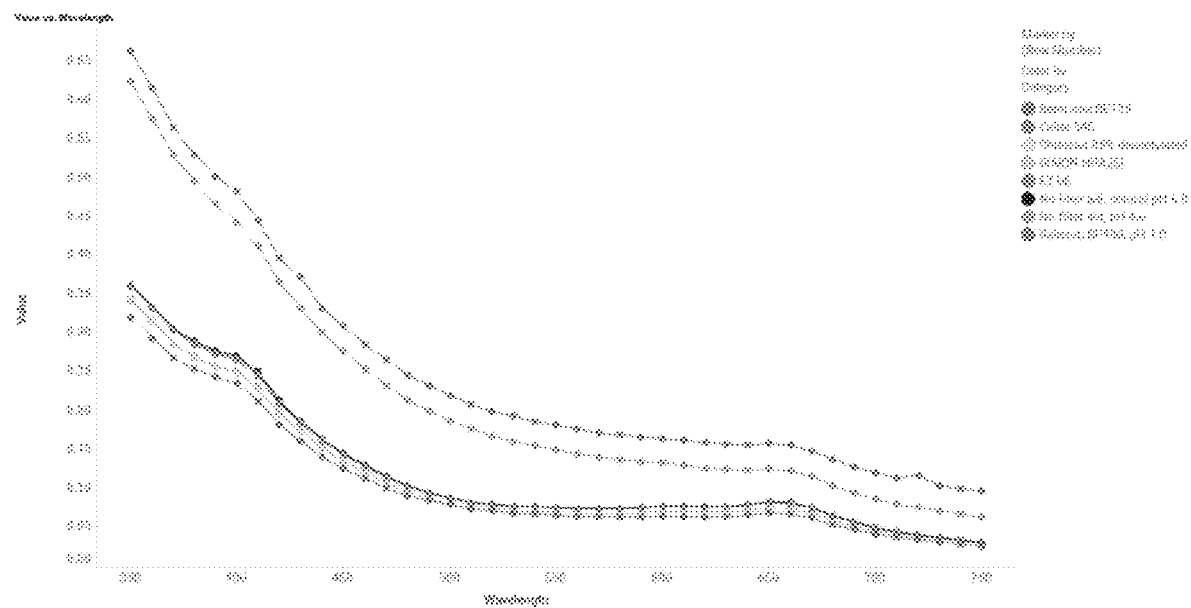
FIG. 15 is a chart showing the absorption spectra of the supernatants from the study in Example 4. The higher pH showed higher absorbance across the board indicating protein is more stable at pH 6 than pH 4. But at pH 4.0 across the various adsorbents tested, bentonite BE125 showed the most decrease in the absorbance. At 350 nm, from top to bottom, the curves are Relisorb SP400; No filter aid, pH4; superimposed EZ DE—Celite 545—No filter aid, pH6; superimposed DIAON HPA25L—Chitosan 85% deacetylated; and Bentonite BE125.

Example 4: Use of an Adsorbent or Flocculant for Preparing a Protein Product Having a Reduced Quantity of a Recombinant Cell Byproduct The protein concentrate prepared as per Example 3 above was further tested with multiple adsorbents and flocculants. The procedure used was as follows: 0.05 g of the test adsorbent or flocculant was weighed out in a 50 mL falcon tube. 5 mL of protein concentrate was added to the test adsorbent or flocculant. The tubes were then placed on roller shaker for 1 hour followed by centrifuging at 3214 g for 30 min. The supernatant was then tested for absorbance, protein and EPS. Each material was tested in duplicate. The list of adsorbents and flocculants tested is as follows. Control (pH 6), control (pH 4), Celite 545, Bentonite BE125, DIAION HPA25L, Chitosan 85% deacetylated, EZ DE (diatomaceous earth), ultrapure diatomaceous earth, Relisorb SP400 (pH 4). The absorbance spectra for this study is shown in FIG. 15. Notably, Relisorb did not work since it bound the protein rather than the impurity at pH 4.0. At higher pH this resin is expected to elute everything.

Figure 16:
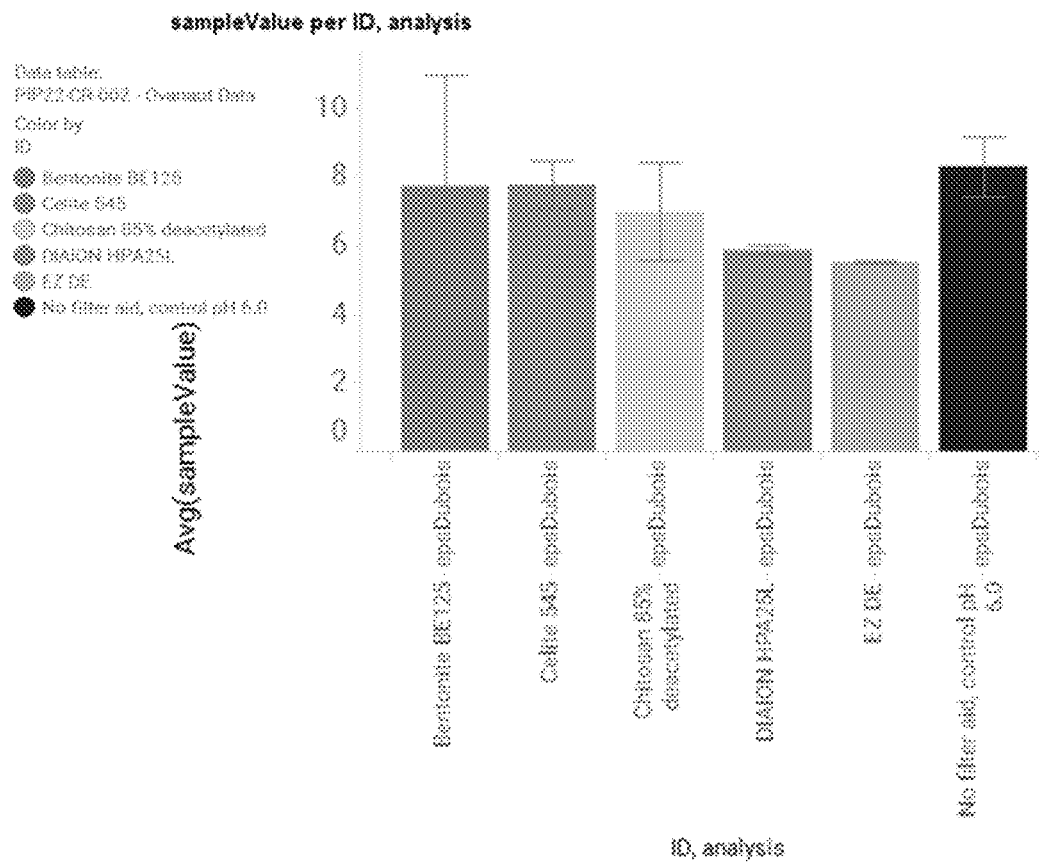
FIG. 16 is a graph showing EPS analysis of the supernatant generated from Example 4.
Figure 17:
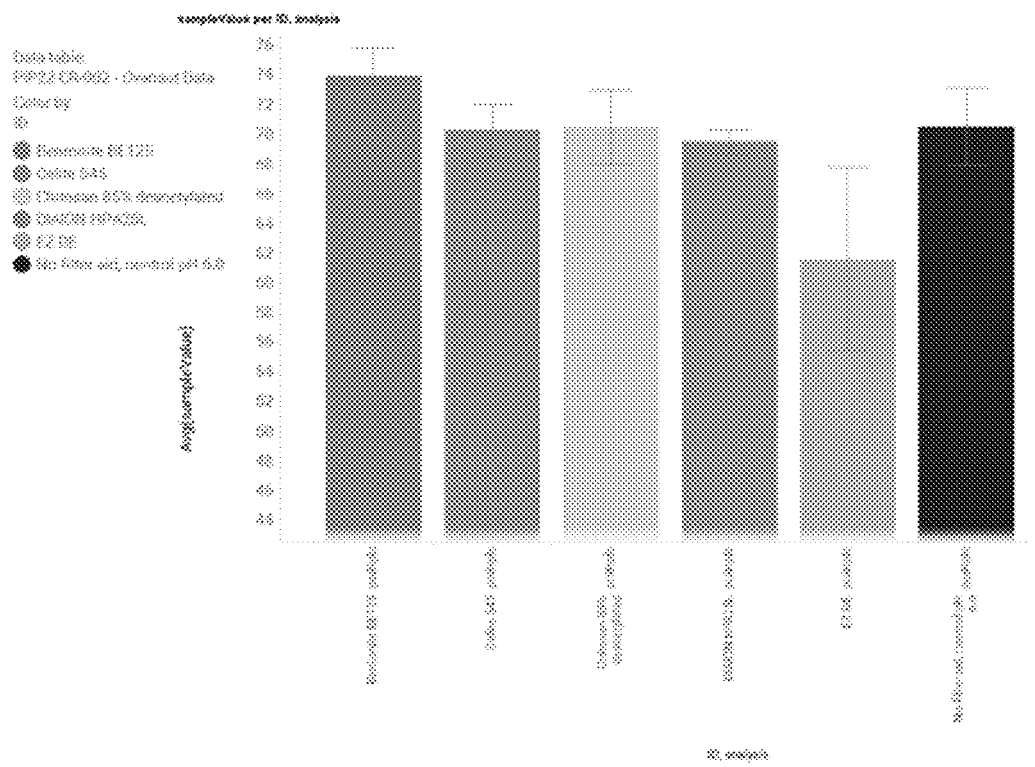
FIG. 17 is a graph showing protein of interest analysis of the supernatants from Example 4.

Further data is shown in FIG. 16 and FIG. 17. These figures show that compared to the control (black) the HPA25L and chitosan adsorb more EPS and almost no protein whereas at pH 4 the SP 400 adsorbs protein and not EPS. Diatomaceous earth (DE) adsorbs both protein and EPS with no differentiation.

Example 5: Use of Flocculants to Extract EPS

A *Pichia Pastoris* strain is grown in fermentation conditions in high-density growth conditions at about pH 5. After about 36 hours of growth under fermentation conditions, the pH is raised to about pH 6, and expression of a protein of interest is induced by the addition of methanol to the culture. At the end of the fermentation, a flocculant is added to the broth at a concentration of 10-100 mg/L. The broth is mixed and held at room temperature or 4° C. for 6 hrs to allow complete utilization of the glucose in the media and the functioning of the flocculant. A coagulant may be added at this point. The fermentation broth is centrifuged (using a bench centrifuge-Avant J18 rotor Bechman Coulter, to remove cells and the EPS like compounds. This is followed by filtration of the supernatant using a 0.2 µm hollow fiber membrane filtration to remove host protein and cell debris. The protein solution s then concentrated using a 5 kDa ultrafiltration membrane to over 30 g/L protein and diafiltered extensively to remove most of the organic and inorganic impurities. The resulting mixture is either microfiltered or heat treated for the final microbial reduction step pre drying. Steps of this method is illustrated in FIG. 4.

Example 6: Use of Enzymes to Digest EPS

A *Pichia Pastoris* strain is grown in fermentation conditions in high-density growth conditions at about pH 5. After about 36 hours of growth under fermentation conditions, the pH is raised to about pH 6, and expression of a protein of interest is induced by the addition of methanol to the culture. At this point an EPS degrading enzyme such as glucanase, is added to the reactor. This will degrade the EPS molecules as they are secreted in the system. The final fermentation broth is centrifuged (using a bench centrifuge-Avant J18 rotor Bechman Coulter, to remove cells. This is followed by filtration of the supernatant using a 0.2 µm hollow fiber membrane filtration to remove host protein and cell debris. The protein solution is then concentrated using a 5 kDa ultrafiltration membrane to over 30 g/L protein and diafiltered extensively to remove most of the organic and inorganic impurities. The EPS degrading enzyme is removed with the biomass in centrifuge and/or in the MF step. The resulting mixture is either microfiltered or heat treated for the final microbial reduction step pre drying. Steps of this method is illustrated in FIG. 2.

Example 7: Use of Adsorbent to Extract EPS

*Pichia Pastoris* strain is grown in fermentation conditions in high-density growth conditions at about pH 5. After about 36 hours of growth under fermentation conditions, the pH is raised to about pH 6, and expression of the protein of interest is induced by the addition of methanol to the culture. At the end of the fermentation, the broth is mixed and held at room temperature or 4° C. for 6 hrs to allow complete utilization of the glucose in the media. The fermentation broth is centrifuged (using a bench centrifuge-Avant J18 rotor Bechman Coulter, to remove cells. The centrate from the centrifuge is then passed on a filter precoated with the adsorbent to remove the EPS like compounds. If a filter is used, then the adsorbent is suspended in water and passed over the filter creating a uniform layer on the filter. This is followed by the passage of the centrate on the filter. This can also be done with a column packed with the same adsorbent. This step is followed by filtration of the supernatant using a 0.2 µm hollow fiber membrane filtration to remove host protein and cell debris. The protein solution is then concentrated using a 5 kDa ultrafiltration membrane to over 30 g/L protein and diafiltered extensively to remove most of the organic and inorganic impurities. The resulting mixture is either microfiltered or heat treated for the final microbial reduction step pre drying. Steps of this method is illustrated in FIG. 3.

Example 8: Removal of Unfavorable Characteristics

A protein concentrate, obtained in the method described in Example 2, was then precipitated by adding ammonium sulfate to reach about 40% w/v concentration in the concentrate solution. The precipitate was then centrifuged (using a bench centrifuge-Avant J18 rotor, Bechman Coulter) to remove the protein. The protein was then resuspended using DI water to a 10% w/v solution. This solution is then diafiltered with DI water to a final conductivity of less than 1 mS/cm. The diafiltered protein is then microfiltered through a 0.2 µm membrane and freeze dried. These proteins are referred to as the "small scale preparations".

For large scale fermentation, at the end of fermentation, the broth was chilled to 8° C. to slow the metabolism of the yeast. Prior to centrifugation, the broth was diluted to reach a packed cell volume of 25% v/v. The yeast cells were then removed by centrifugation and supernatant was stored and moved to the next step. This step is completed within 8 hours of completing the fermentation and can begin before chilling is complete. An appropriate disc stack centrifuge with large enough surface area and solid capacity is used for this purpose. The bulk OD600 measurement of the supernatant to indicate good separation is preferably <0.9 AU. The centrate was collected for further clarification through the 0.2 µm filtration. The 0.2 µm filtration will run in a tangential flow mode with both concentration and dia-filtration steps. During the concentration step, the retentate volume is reduced by about 6-9×. To achieve higher yields the retentate is continuously diafiltered with ten diavolumes of water. The permeate from the 0.2 µm TFF is concentrated 6-8× from its initial volume to around 50 g/L protein concentration. The final retentate was a dark green in color. This retentate was then diafiltered with 6-8 DVs of DI water. The diafiltered retentate is then sterile filtered using a 0.2 μm MF filter and spray dried with inlet temp around 165° C. and outlet temp not exceeding 80° C. The membranes may be hydrophilic polyethylene sulfone designed for protein applications. The temperature was maintained at 10° C. throughout the process. These proteins are referred to as the "large scale preparations".

The above processes result in a dark green solution predrying. To decolorize and deodorize it, an oxidation step may be utilized. The pH of the retentate before diafiltration was reduced to 4 using 85% v/v phosphoric acid. Then, 35% v/v hydrogen peroxide was added slowly to saturate the final solution to a 3% v/v hydrogen peroxide mixture. The mixture was then held in a tank for 6 hrs while mixing slowly to prevent foam outs. The pH was then changed back to 6 using concentrated sodium hydroxide followed by the diafiltration, sterile filtration and drying. These protein samples are referred to as the "Example A" samples.

The samples from the end of fermentation and end of the process of Example A were analyzed using GC-MS. The prominent flavor and odor compounds observed are listed in the Table 6, below:

TABLE 6

List of prominent flavor/odor causing compounds at end of fermentation and purification.

| Source | Chemical class | Compound | BP | solubility alcohols | Typical source/use |
|---|---|---|---|---|---|
| Observed at end of fermentation | Alcohol | 1-Hexanol, 2-ethyl- | no—180 C. | yes | common in plant fruit wines |
| | | Benzyl alcohol | no—205 C. | yes | common in plant fruit wines |
| | Aldehydes | 2-Propanone | yes 56 C. | yes | acetone-industrial solvent |
| | Ketone | 2-Butanone | no—azeotrope | yes | Industrial solvent |
| | | 1-Dodecene | yes—79 C. | yes | known Fermentation volatile |
| | Ester | Propanoic acid, 2-methyl-, 3-hydroxy-2,4,4-trimethylpentyl ester | no—249 C. | yes | known Fermentation volatile |
| Observed post purification step | Aldehydes | Butanal, 3-methyl- | yes—94 C. | yes | Isovaleraldehyde |
| | Ketone | 2-Undecanone | no—231 C. | yes | common in plant fruit wines |
| | Alcohol | Benzene ethanol | no—221 C. | yes | phenylethanol—auto antibiotic produced by fungi |
| | Acid | Nonanoic acid | no—254 C. | yes | pelargonic acid—herbicide; rancid odor, treatment of seizures |
| | Aromatics | chlorotoluene | no—162 C. | yes | antibacterial irritating flavor |

The resulting protein retentate from the small scale preparation and the large scale preparations was adjusted for pH and loaded on to a chromatography column. This column was packed with Cation exchange resin (SP400, Mitsubishi Chemicals, Japan). The chromatography steps were carried out with an AKTA Explorer 900 (GE Healthcare Life Sciences) and the Unicorn interface software (version 5.11) at approximately 22° C. in a down-flow mode. the chromatography method generally consisted of an equilibration step, a load (flowthrough) step, a wash step to remove non-bound protein, an elution step to remove product, a cleaning in place (CIP) step and regeneration step. The column volumes of elution, at each step and the buffer used is shown in the above Table 4 and The elution profile is shown in FIG. 12.

This elution fraction from the column is then concentrated and diafiltered to remove the elution buffer salts. This stream is then microfiltered using a 0.2 μm membrane and dried. These samples are referred to as the "Example B" samples.

The oxidized samples and non-oxidized samples were then tested with GC-MS using a polar, Stabilwax-DA column. The sample prep used was SPME and the analysis consisted of the MS data as well as the human olfactory odor testing. See Table 7, below for results for the small-scale protein preparations:

TABLE 7

GC MS data for samples generated in the lab setup (small scale preparations) using oxidation and chromatography methods.

| compound | odor property | Example A | Example B |
|---|---|---|---|
| 2-methylpropanal | dark chocolate, malty | Weak | Very weak |
| 2-methylbutanal | dark chocolate, malty | Very weak | Weak |
| 3-methylbutanal | dark chocolate, malty | Weak | Medium |
| 2,3-butanedione | buttery, creamy | Weak | Very weak |
| 1-hexen-3-one | skunky, rubbery, plastic | Weak | Weak |
| 1-octen-3-one | earthy, mushroom | Medium | Weak |
| "unknown" | milky, cooked milk, potato | Weak | Very weak |
| (E)-2-nonenal | stale, green, hay | Very weak | Medium |
| p-cresol | animal stable, barnyard | Very weak | Very weak |
| acetaldehyde | pungent, ethanolic | Very weak | Very weak |

See Table 8, below for results for the large-scale protein preparations:

TABLE 8

GC MS data for samples generated in the lab setup (small scale preparations) using oxidation and chromatography methods.

| compound | odor property | Example A | Example B |
|---|---|---|---|
| 2-methylpropanal | dark chocolate, malty | Strong | Medium |
| 2-methylbutanal | dark chocolate, malty | Strong | Medium |
| 3-methylbutanal | dark chocolate, malty | Medium | Weak |
| 2,3-butanedione | buttery, creamy | Medium | Weak |
| 1-hexen-3-one | skunky, rubbery, plastic | Weak | Weak |
| 1-octen-3-one | earthy, mushroom | Medium | Weak |
| "unknown" | milky, cooked milk, potato | Weak | Weak |
| (E)-2-nonenal | stale, green, hay | Very weak | Weak |
| p-cresol | animal stable, barnyard | Weak | Very weak |
| acetaldehyde | pungent, ethanolic | Weak | Very weak |

Most of the compounds listed in Table 7 are reduced when comparing the Example A samples to the Example B samples. This is even clearer in Table 8, with the large scale preparations.

The Example B samples generated above were further reprocessed using various treatments to check the improvement in sensory characteristics. The treatments tested were as follows:

Ethanol wash: The spray dried protein powder was resuspended in 10% v/v ethanol solution to reach a solids concentration of 50 g/L. The solution was stirred for 1 hour at ambient temperature using a magnetic stirrer and then diafiltered with 4-5 DVs of DI water on a 5 kDa membrane. The retentate was sterile filtered and dried.

Ion exchange (IEX): The spray dried protein powder was resuspended in DI water to reach a solids concentration of 50 g/L. The process described in example 5 was repeated with this protein solution.

Heat and Vacuum: The spray dried protein powder was resuspended in DI water to reach a solids concentration of 50 g/L. The protein solution was then heated to 50-58 C and maintained for 1 hr under low vacuum (75-150 torr). The solution was then sterile filtered and dried.

IEX, heat and vacuum: This was an orthogonal approach to combine various purification methods together. The product from the example 5 was then resuspended in DI water to reach a solids concentration of 50 g/L. The protein solution was then heated to 50-58 C and maintained for 1 hr under low vacuum (75-150 torr). The solution was then sterile filtered and dried.

Figure 18:
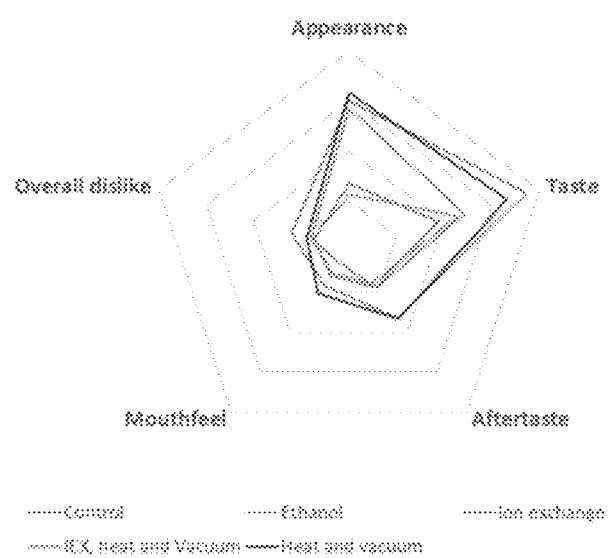
FIG. 18 compares controls and various reprocessing methods. A curve surrounding the central core of the pentagon is the most neutral and preferred protein product. For data relating to taste (pointing towards the right of the pentagon), the worst performer is the control; then heat and vacuum; then IEX, heat, and vacuum; then ethanol; and the best performer was ion exchange. For data relating to appearance (at the top), the worst performer was the heat and vacuum; then control; then IEX, heat, and vacuum; then ion exchange; and the best performer was ethanol.

The sensory analysis performed on these samples based on appearance, mouthfeel and aftertaste of a 6% w/v solution in water was analyzed in FIG. 18. The ion exchange process of the non-oxidized preparations yielded the best version of the reprocessed control. The center of the graph represents the sensory profile of water.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

What is claimed is:

1. A method for preparing a protein product having a reduced quantity of a plurality of recombinant cell byproducts, the method comprising steps of:
   (1) obtaining a composition comprising a recombinant protein and a plurality of recombinant cell byproducts comprising at least one human-detectable flavor or odor selected from the group consisting of an acid, an alcohol, an aldehyde, an aromatic, an ester, and a ketone;
   (2) processing the composition under conditions that separate the recombinant protein from the plurality of recombinant cell byproducts, thereby obtaining a separated recombinant protein,
   wherein the processing step comprises contacting the composition with an anionic resin that reversibly attaches to the recombinant protein and does not substantially attach to the plurality of recombinant cell byproducts; and
   (3) collecting the separated recombinant protein, thereby obtaining a protein product having a reduced quantity of the plurality of recombinant cell byproducts;
   wherein the composition comprising the recombinant protein and the plurality of recombinant cell byproducts is a cell culturing medium which contained recombinant cells that secreted the recombinant protein and contained the plurality of recombinant cell byproducts.

2. The method of claim 1, wherein the composition comprising the recombinant protein and the plurality of recombinant cell byproducts has a pH greater than the isoelectric point (pI) of the recombinant protein.

3. The method of claim 1, wherein the anionic resin is one or more of Capto Q resin, a DEAE resin, a resin with trimethyl aminoethyl groups, a resin with triethyl aminoethyl groups, and a resin with quaternary amine groups.

4. The method of claim 1, wherein the anionic resin is a component of a chromatography system which operates in a batch mode with an axial flow column or a radial flow column or a centrifugal column or by use of a membrane chromatography column, or a chromatography system which operates in a continuous mode comprising multiple columns in parallel, with feed to the column or columns being switchable such that equilibration, loading, eluting, and/or cleaning steps in a chromatography process using the column or columns occur contemporaneously.

5. The method of claim 4, wherein the anionic resin is a component of a chromatography system which operates in a continuous mode and comprises a simulated moving bed (SMB) or an ion chromatography system.

6. The method of claim 1, wherein the method further comprises a step of treating the composition comprising the recombinant protein and the plurality of recombinant cell byproducts to remove spent biomass including recombinant cells and/or to remove small non-protein molecules.

7. The method of claim 6, wherein the step of treating to remove small non-protein molecules comprises a step that concentrates the composition comprising the recombinant protein and the plurality of recombinant cell byproducts.

8. The method of claim 1, wherein the recombinant cell byproducts comprise one or more of (E)-2-nonenal; 1-dodecene; 1-hexanol, 2-ethyl-; 1-hexen-3-one; 1-octen-3-one; 2,3-butanedione; 2-butanone; 2-methylbutanal; 2-methylpropanal; 2-propanone; 2-undecanone; 3-methylbutanal; acetaldehyde; benzene ethanol; benzyl alcohol; butanal, 3-methyl-; chlorotoluene; nonanoic acid; p-cresol; propanoic acid; and 2-methyl-, 3-hydroxy-2,4,4-trimethylpentyl ester.

9. The method of claim 1, wherein the protein product having a reduced quantity of the plurality of recombinant cell byproducts has an at least 80% reduction in the quantity of the recombinant cell byproducts relative to the composition comprising the recombinant protein and the plurality of recombinant cell byproducts.

10. The method of claim 9, wherein less than about 5% of the weight of the protein product comprises the recombinant cell byproducts.

11. The method of claim 1, wherein the recombinant cells that expresses the recombinant protein and the plurality of recombinant cell byproducts are selected from fungal cells, bacterial cells, plant cells, insect cells, and mammalian cells.

12. The method of claim 11, wherein the fungal cells are filamentous fungi or yeast.

13. The method of claim 11, wherein the recombinant cells are selected from *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*,

*Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium* camemberti, *Penicillium canescens*, *Penicillium chrysogenum*, *Penicillium* (*Talaromyces*) *emersonii*, *Penicillium* funiculo sum, *Penicillium purpurogenum*, *Penicillium* roqueforti, *Pleurotus* spp., *Pleurotus* ostreatus, *Pseudomonas* spp., *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, and *Trichoderma* vireus.

14. The method of claim 1, wherein the recombinant protein is an enzyme, a nutritive protein, a food ingredient, or a food additive.

15. The method of claim 1, wherein the recombinant protein is an egg-white protein selected from ovalbumin (OVA), ovomucoid (OVD), ovotransferrin (OVT), lysozyme (OVL), ovomucin, ovoglobulin G2, ovoglobulin G3, ovoinhibitor, ovoglycoprotein, flavoprotein, ovomacroglobulin, ovostatin, cystatin, avidin, ovalbumin related protein X, and ovalbumin related protein Y, and any combination thereof.

16. The method of claim 15, wherein the egg-white protein has a sequence that at least 80% identical to the egg-white protein naturally produced in a bird.

17. The method of claim 16, wherein the bird is a chicken, a quail, a turkey, a turkey vulture, a hummingbird, a duck, an ostrich, a goose, a gull, a guineafowl, a pheasant, or an emu.

18. The method of claim 1, wherein the protein product having a reduced quantity of a plurality of recombinant cell byproducts is formulated into a consumable composition selected from a food product, a beverage product, or a dietary supplement.

19. A consumable composition comprising the protein product having the reduced quantity of the plurality of recombinant cell byproducts prepared by the method of claim 1, wherein the reduced quantity of the plurality of recombinant cell byproducts comprises at least 80% less human-detectable flavor or odor byproducts than the amount present in the composition comprising the recombinant protein and the plurality of recombinant cell byproducts of step (1) of claim 1.

20. The method of claim 1, wherein the cell culturing medium comprises at least one recombinant cell that secreted the recombinant protein and the plurality of recombinant cell byproducts.

21. A method for preparing a protein product having a reduced quantity of a plurality of recombinant cell byproducts, the method comprising steps of:
   (1) obtaining a composition comprising a recombinant protein and a plurality of recombinant cell byproducts comprising at least one human-detectable flavor or odor; wherein the composition comprising the recombinant protein and the plurality of recombinant cell byproducts is a cell culturing medium which contains or contained recombinant cells that secreted the recombinant protein and the plurality of recombinant cell byproducts;
   (2) processing the composition under conditions that separate the recombinant protein from the plurality of recombinant cell byproducts to obtain a separated recombinant protein, wherein the processing step comprises contacting the composition with an anionic resin that reversibly attaches to the recombinant protein and does not substantially attach to the plurality of recombinant cell byproducts;
   (3) concentrating and/or diafiltering the separated recombinant protein to produce a protein-containing composition having a selected pH and/or ionic condition suitable for the consumable composition; and
   (4) collecting the separated recombinant protein, thereby obtaining a protein product having a reduced quantity of the plurality of recombinant cell byproducts;
   wherein the composition comprising the recombinant protein and the plurality of recombinant cell byproducts, the protein-containing composition having a selected pH and/or ionic condition suitable for the consumable composition and/or the protein product having a reduced quantity of the plurality of recombinant cell byproducts further undergoes a heat treatment, and optionally microfiltration and/or drying;
   wherein the heat treatment and optionally microfiltration and/or drying separates the recombinant protein and the recombinant cell byproducts, wherein heat from the heat treatment is applied at a temperature and duration such that the recombinant cell is byproducts are volatized and gaseous recombinant cell is byproducts are removed.

22. The method of claim 21, wherein a vacuum is applied contemporaneously with the heat treatment and the vacuum facilitates removal of the gaseous recombinant cell byproducts.

23. The method of claim 21, wherein the temperature of the heat treatment is up to 80° C.

24. The method of claim 21, wherein the composition comprising the recombinant protein and the plurality of recombinant cell byproducts, the protein-containing composition having a selected pH and/or ionic condition, and/or the protein product having a reduced quantity of the plurality of recombinant cell byproducts further undergoes an oxidation step.

25. The method of claim 24, wherein the oxidation step comprises the addition of hydrogen peroxide.

26. The method of claim 1, wherein the recombinant cell byproducts further comprise an exopolysaccharide (EPS).

27. The method of claim 26, wherein the EPS
   (i) has an apparent size of about 13 kDa to about 27 kDa as characterized by a size exclusion chromatography column;
   (ii) comprises mannose and/or comprises N-acetylglucosamine and/or glucose;
   (iii) comprises about 91 mol % mannose, about 5 mol % N-acetylglucosamine, and about 3 mol % glucose as analyzed by gas chromatography in tandem with mass spectrometry;
   (iv) comprises an $\alpha(1,6)$-linked backbone with $\alpha(1,2)$-linked branches and/or a$(1,3)$-linked branches; and/or
   (v) is a mannan.

28. The method of claim 26, wherein the method further comprises one or more of steps of:
   (i) contacting the EPS with one or more cation exchange resins that reversibly attach to the recombinant protein and do not substantially attach to the EPS,
   (ii) contacting the EPS with an enzyme that digests the recombinant protein or the EPS,
   (iii) contacting the EPS with an adsorbent that reversibly attaches to the EPS and does not substantially attach to the recombinant protein, and/or (iv) contacting the EPS with a flocculant that attaches to the EPS and does not substantially attach to the recombinant protein.

29. The method of claim 21, wherein the temperature of the heat treatment is from about 50° C. to about 60° C.

30. A method for preparing a protein product having a reduced quantity of a plurality of recombinant cell byproducts comprising a human-detectable flavor or odor, the method comprising steps of:
(1) obtaining a composition comprising a recombinant protein and a plurality of recombinant cell byproducts comprising at least one human-detectable flavor or odor selected from the group consisting of an acid, an alcohol, an aldehyde, an aromatic, an ester, and a ketone;
(2) processing the composition under conditions that separate the recombinant protein from the plurality of recombinant cell byproducts, thereby obtaining a separated recombinant protein, wherein the processing step comprises contacting the composition with an anionic resin that reversibly attaches to the recombinant protein and does not substantially attach to the plurality of recombinant cell byproducts; and
(3) collecting the separated recombinant protein, thereby obtaining a protein product having a reduced quantity of the plurality of recombinant cell byproducts.

* * * * *

UNITED STATES PATENT AND TRADEMARK OFFICE
CERTIFICATE OF CORRECTION

PATENT NO. : 11,718,644 B2
APPLICATION NO. : 18/050213
DATED : August 8, 2023
INVENTOR(S) : Kale et al.

Page 1 of 1

It is certified that error appears in the above-identified patent and that said Letters Patent is hereby corrected as shown below:

On the Title Page

Item (72), in Column 1, in "Inventors", Line 2, delete "Francsico," and insert -- Francisco, --, therefor.

In the Claims

In Column 66, in Claim 11, Line 56, delete "expresses" and insert -- express --, therefor.

In Column 68, in Claim 21, Line 25, delete "cell is" and insert -- cell --, therefor.

In Column 68, in Claim 21, Line 26, delete "cell is" and insert -- cell --, therefor.

In Column 68, in Claim 27, Line 45, after "EPS" insert -- : --.

In Column 68, in Claim 27, Line 56, delete "a(1,3)" and insert -- α(1,3) --, therefor.

In Column 68, in Claim 28, Line 59, delete "of steps of:" and insert -- steps of: --, therefor.

Signed and Sealed this
Twenty-third Day of April, 2024

*Katherine Kelly Vidal*

Katherine Kelly Vidal
*Director of the United States Patent and Trademark Office*